United States Patent
Napper et al.

(10) Patent No.: US 6,479,265 B1
(45) Date of Patent: *Nov. 12, 2002

(54) CATALYTIC ANTIBODIES WHICH HYDROLYZE PRIMARY AMIDES AND METHODS FOR ELICITING AND USE OF SUCH ANTIBODIES

(75) Inventors: Andrew Napper, Natick, MA (US); Richard C. Titmas, Damascus; Mark Martin, Gaithersburg, both of MD (US); Wonpyo Hong, Hockessin, DE (US)

(73) Assignee: Igen International, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/524,920

(22) Filed: Sep. 8, 1995

Related U.S. Application Data

(63) Continuation of application No. 08/052,490, filed on Apr. 23, 1993, now abandoned.

(51) Int. Cl.$^7$ ................................................. C12N 9/00
(52) U.S. Cl. .................................................. 435/188.5
(58) Field of Search ........................ 435/188.5; 424/94.6

(56) References Cited

U.S. PATENT DOCUMENTS 5,126,258 A * 6/1992 Lerner et al. ............. 435/188.5

OTHER PUBLICATIONS

Gallacher, G., et al., (1992) Biochem. J. 284, 625–680.*
"Observations in the Interface Between Immunology and Chemistry" by Lerner et al. 3 *Chemtracts—Organic Chemistry* 1–36 (1990).
"Recent Advances in Catalytic Antibodies" by Scanlon et al. 332 *Phil. Trans. R. Soc. Lond. B.* 157–164 (1991).
"Catalytic Antibodies" by Schultz et al. *Chem. Eng. News* 26–40 (May 28, 1990).
"Catalytic Antibodies—A New Direction In Enzyme Design" by Powell et al. 3 *Protein Eng.* 69–75 (1989).
"A Semisynthetic Catalytic Antibody" by Pollack et al. 111 *J. Am. Chem. Soc.* 1929–1931 (1989).
"Designer and Catalytic Antibodies" by Mayforth et al. 323 *N. Eng. J. Med.* 173–178 (1990).
"Catalytic Antibodies" by Shokat et al. 8 *Ann. Rev. Immunol.* 335–363 (1990).
"Induction of an Antibody That Catalyzes the Hydrolysis of an Amide Bond" by Janda et al. 241 *Science* 1188–1191 (1988).
"Principles of Antibody Catalysis" by Lerner et al. 9 *BioEssays* 107–112 (1988).
"Catalytic Antibodies" by Lerner et al. 258 *Sci. Am.* 58–70 (1988).

"A Protein–cutting Antibody Could Destroy the Coat of a Virus" by Schmeck *The New York Times* (Jan. 27, 1987).
"Biochemists Make the First Catalytic Antibodies . . . " by Scott *N. Scientist* 31 (Feb. 12, 1987).
"Making Antibodies Work Like Enzymes" by Marx 234 *Science* 1497–8 (1986).
"Catalytic Antibodies Open Up New Strategy for Protein Engineering" by Baum 65 *Chem. Eng. News* 30–33 (1987).
"Hydrolysis of a Peptide Bond in Neutral Water" by Kahne et al. 110 *J. Am. Chem. Soc.* 7529–7534 (1988).
"Catalytic Antibodies" by Tramontano et al. 234 *Science* 1566–1569 (1986).
"Antibody Catalysis Approaching the Activity of Enzymes" by Tramontano et al. 110 *J. Am. Chem. Soc.* 2282–2286 (1988).
"AB INITIO Structural Comparison Between the Tetrahedral Intermediates and the Phosphorus–containing Analogues in the Ester and Amide Hydrolysis" by Teraishi et al. 33 *Tet. Lett.* 7153–7156 (1992).
*Chemical Kinetics* by Laidler Harper & Row 113 (1987).
"Sequence–Specific Peptide Cleavage Catalyzed by an Antibody" by Iverson et al. 243 *Science* 1184–1188 (1989).
"Antibody–Catalyzed Rearrangement of the Peptide Bond" by Gibbs et al. 258 *Science* 803–805 (1992).
"Catalytic Hydrolysis of Vasoactive Intestinal Peptide by Human Autoantibody" by Paul et al. 244 *Science* 1158–1162 (1989).

(List continued on next page.)

*Primary Examiner*—Charles L. Patterson, Jr.
(74) *Attorney, Agent, or Firm*—Kramer Levin Naftalis & Frankel LLP; Barry Evans, Esq.

(57) ABSTRACT

Described and claimed are compounds of the formula

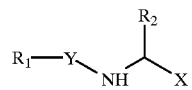

wherein:
  Y is a polypeptide,
  $R_1$ is bonded to the N-terminus of Y and is hydrogen or a branched or linear, substituted or unsubstituted, $C_{1-21}$ alkyl, alkene, or alkyne group,
  $R_2$ is a side chain of a naturally occuring amino acid, and X is

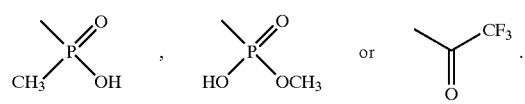

Such compounds are useful as haptens and immunogens for the elicitation of antibodies which catalytically enhance the rate of formation or hydrolysis of primary amide bonds. Also described and claimed are methods employing the compounds and antibodies.

4 Claims, 14 Drawing Sheets

OTHER PUBLICATIONS

"The Free Energy Change in Hydrolytic Reactions: The Non–ionized Compound Convention" by Carpenter 82 *J. Am. Chem. Soc.* 1111–1122 (1960).

*Reaction Kinetics* by Laidler Pergamon Press 42–43.

*Catalysis in Chemistry and Enzymology* by Jencks McGraw–Hill 193–194 (1969).

"The Biosynthesis of Neuropeptides: Peptide α–Amidation" by Eipper et al. 15 *Ann. Rev. Neurosci.* 57–85 (1992).

"Late Reactions in the Processing of Peptide Precursors: Stepwise Cleavage of Dipeptides and Formation of Terminal Amides" by Kreil, vol. 2 *The Enzymology of Post–Translational Modification of Protein* Academic Press 41–51 (1980).

"Strategies for the Biosynthesis of Bioactive Peptides" by Mains et al. 6 *Trends in Neurosciences* 229–35 (1983).

*Hormones in Blood* by Gray et al. vol. 5 Academic Press 42 (1983).

"The Calcitonin Gene Peptides: Biology and Clinical Relevance" by Zaidi et al. 28 *Crit. Rev. Clin. Lab. Sci.* 109–174 (1990).

"CGRP Antagonist Activity of Short C–Terminal Fragments of Human αCGRP, CGRP(23–37) and CGRP(19–37)" by Rovero et al. 13 *Peptides* 1025–1027 (1992).

"Biological Effects of Human Gastrin I and II Chemically Modified at the C–Terminal Tetrapeptide Amide" by Gallerand et al. 13 *Peptides* 519–525 (1992).

*Hormones in Blood* by Gray et al. vol. 5 Academic Press 200–201 (1983).

"Small Cell Carcinoma of the Lung: Clinical and Biologic Aspects" by Viallet et al. 11 *Crit. Rev. Onc./Hem.* 109–135 (1991).

"Characterization, in Some Human Breast Cancer Cell Lines, of Gastrin–releasing Peptide–like Receptors Which are Absent in Normal Breast Epithelial Cells" by Giacchetti et al. 46 *Int. J. Cancer* 293–298 (1990).

"Phase I Study of an Anti Gastrin Releasing Peptide (GRP) Monoclonal Antibody in Patients with Lung Cancer" by Mulshine et al. 9 *Proc. Am. Soc. Clin.* 230 (1990).

"CD10/Neutral Endopeptides 24:11 Hydrolyzes Bombesin–line Peptides and Regulates the Growth of Small Cell Carcinomas of the Lung" by Shipp et al. 88 *Proc. Natl. Acad. Sci. USA* 10662–10666 (1991).

"[Psi $^{13,14}$] Bombesin Analogues Inhibit Growth of Small Cell Lung Cancer in Vitro and in Vivo" by Mahmoud et al. 51 *Cancer Res.* 1798–1802 (1991).

"Metabolic Stability and Tumor Inhibition of Bombesin/GRP Receptor Antagonists" by Davis et al. 13 *Peptides* 401–407 (1992).

"Progress in the Development of Potent Bombesin Receptor Antagonists" by Jensen et al. 12 *Trends Pharm. Sci.* 13–19 (1991).

"Micelle–Bound Conformations of a Bombesin/Gastrin Releasing Peptide Receptor Angonist and an Antagonist by Two–Dimensional NMR and Restrained Molecular Dynamics" by Malikayil et al. 31 *Biochemistry* 7043–7049 (1992).

"R–Agent Induction and Intensive Asparaginase Therapy for Treatment of Childhood Acute Lymphoblastic Leukemia" by Clavell et al. 315 *N. Eng. J. Med.* 657–663 (1986).

"Bombesin–like Peptides Can Function as Autocrine Growth Factors in Human Small–cell Lung Cancer" by Cuttitta et al. 316*Nature* 823–826 (1985).

"Cell Biology and Molecular Biology of Small Cell and Non–small Cell Lung Cancer" by Gazdar 2 *Curr. Opin. Oncol.* 321–327 (1990).

"Generation of Cytotoxic Agents by Targeted Enzymes" by Senter et al. 4 *Bioconj. Chem.* 3–9 (1993).

"Solid–phase Synthesis of N–Methyl—and N–Ethylamides of Peptides Using Photolytically Detachable ((3–Nitro–4–((alkylamino)methyl)benzamido)methyl)polystyrene Resin" by Ajayaghosh et at. 55 *J. Org. Chem.* 2826–2829 (1990).

"Practical Approach to Solid–phase Synthesis of C–terminal Peptide Amides Under Mild Conditions Based on a Photolysable Anchoring Linkage" by Hammer et al. 36 *Int. J. Peptide Protein Res.* 31–45 (1990).

"Semisynthesis of Human Growth Hormone–Releasing Factors by α–Amidating Enzyme Catalyzed Oxidation of Glycine–Extended Precursors" by Bongers et al. 5 *Peptide Research* 183–189 (1992).

"Peptide Amidation by Chemical Protein Engineering. A Combination of Enzymatic and Photochemical Synthesis" by Hendriksen et al. 114 *J. Am. Chem. Soc.* 1876–1877 (1992).

"Conformation—Activity Relationship of Tachykinin Neurokinin A (4–10) and of Some [Xaa$^8$] Analogues" by Saviano et al. 30 *Biochemistry* 10175–10181 (1991).

"Substance K: A Novel Mammalian Tachykinin That Differs from Substance P in its Pharmacological Profile" by Nawa et al. 34 *Life Sci.* 1153–1160 (1984).

"Enzymes in Organic Solvents" by Russell 17 *Biochem. Sci. Trans.* 1145 (1990).

"Inhibitor–induced Enzyme Activation in Organic Solvents" by Russell et al. 263 *J. Biol. Chem.* 11624–11626 (1988).

"Antibody–Antigen Binding in Organic Solvents" by Russell et al. 158 *Biochem. Biophys. Res. Commun.* 80–85 (1989).

"Antibody Catalysis in Low Water Content Media" by Ashley et al. 57 *J. Am. Chem. Soc.* 6691–6693 (1992).

Ray, M.V.L., et. al, (1993) Bio/Technology 11, 64–70.

"Catalysis of a Stereospecific Bimolecular Amide Synthesis by an Antibody" Benkovic et al. 85 *Proc. Natl. Acad. Sci. USA* 5355–5358 (1988).

"Antibody Catalysis of Bimolecular Amide Formation" by Janda et al. 110 *J. Am. Chem. Soc.* 4835–4837 (1988).

* cited by examiner

| COMPOUND | R₁ | R₂ | * |
|---|---|---|---|
| 1, NA-1 | maleimide-(CH₂)₅ | P(=O)(O)CH₃ | D/L |
| 2 | maleimide-(CH₂)₅ | C(=O)CF₃ | D/L |
| 3, RT-2 | maleimide-(CH₂)₅ | P(=O)(O)OCH₃ | D/L |
| 4 | H₃C-C(=O)-NH-(CH₂)₅ | P(=O)(O)CH₃ | D |
| 5 | H₃C-C(=O)-NH-(CH₂)₅ | P(=O)(O)CH₃ | L |
| 6 | H₃C | P(=O)(O)OCH₃ | D/L |
| 7 | H₃C | C(=O)CF₃ | D/L |
| 8, WH-2 | maleimide-(CH₂)₅ | C(=O)CF₃ | D/L |

| COMPOUND | R₁ | R₂ | * |
|---|---|---|---|
| 9 | dansyl-NH | $CNH_2$ (C=O) | L |
| 10 | dansyl-NH-(CH₂)₅ | $CNH_2$ (C=O) | D |
| 11 | dansyl-NH-(CH₂)₅ | $COCH_3$ (C=O) | L |
| 12 | dansyl-NH-(CH₂)₅ | $COCH_3$ (C=O) | D |
| 13 | H₃C | $CNH_2$ (C=O) | L |
| 14 | H₃C | $CNH_2$ (C=O) | D |
| 15 | H₃C | $COCH_3$ (C=O) | L |
| 16 | H₃C | $COCH_3$ (C=O) | D |

10

34

1) CF$_3$I/DMF/-20°C
   ACTIVATED ZINC DUST
2) DESS MARTIN PERIODINANE

CATALYTIC ANTIBODIES WHICH HYDROLYZE PRIMARY AMIDES AND METHODS FOR ELICITING AND USE OF SUCH ANTIBODIES

CROSS REFERENCE TO RELATED APPLICATIONS

This application is a file wrapper continuation of U.S. Ser. No. 08/052,490, filed Apr. 23, 1993, now abandoned.

FIELD OF THE INVENTION

This invention relates to analogs of primary amide bonds and methods of using such analogs such as for eliciting catalytic antibodies for hydrolysis of primary amide bonds. The invention also relates to catalytic antibodies capable of catalyzing the hydrolysis or formation of primary amide bonds.

This invention further relates to novel methods for using such catalytic antibodies as therapeutic agents wherein said catalytic antibodies cause hydrolysis of primary amide bonds of peptides and proteins.

This invention also relates to novel methods for using such catalytic antibodies as catalysts for hydrolysis of formation of primary amide bonds in the synthesis of chemicals.

Still further, this application relates to novel methods for selecting or screening for catalytic activity by catalytic antibodies in samples containing antibodies as well as other biological molecules. Such methods for selecting or screening are rapid and efficient and thus, allow the routine screening of larger numbers of potential catalytic antibodies.

BACKGROUND OF THE INVENTION

Various documents are cited parenthetically throughout the text of this disclosure, with full citation to these documents appearing as a list immediately preceding the claims. Other documents are cited parenthetically, in full, throughout the text of this disclosure. These documents pertain to the field of this invention, and each of these documents is hereby incorporated herein by reference.

One of the most frequently cited goals of catalytic antibody research is the generation of antibodies capable of efficient, specific hydrolysis of amide bonds (1–14). This goal partly results from the scientific challenge of generating an antibody to catalyze a relatively kinetically inert reaction and partly from the potentially vast range of practical applications for proteolytic antibodies.

Until now, no haptens have been designed which have demonstrably elicited antibodies that hydrolyze unactivated amides without cofactor assistance.

The difficulty in eliciting amide-hydrolyzing antibodies stems primarily from the difficulties associated with screening the antibodies for catalysis. The uncatalyzed rate ($k_{uncat}$) of amide hydrolysis (with a half-life on the order of 7 years at neutral pH (15)) is much slower than that of typical esters (16), carbonates (17), or activated amides (8, 18). Correspondingly, it is much more difficult to detect antibodies that catalyze amide hydrolysis. If two separate reactions of different uncatalyzed rates ($k_{uncat}$) are catalyzed by two antibodies with identical rate enhancements ($k_{cat}/k_{uncat}$), it will be more difficult to detect the antibody that is slower in absolute terms ($k_{cat}$). There are two main reasons for this. One reason is that in the slower reaction there will be fewer turnovers per unit of time and the assay system must be able to detect extremely low levels of formed product. The second reason is that reactions with slower $k_{uncat}$ values typically require longer periods of antibody-substrate incubation (days or weeks) than do faster reactions (minutes or hours). Long incubation periods may lead to false results because of the possible appearance of by-products, the antibody may denature, especially at non-neutral pH values, and traces of adventitious enzymes may catalyze the reaction in question.

As mentioned above, until now no catalytic antibodies have been generated that are capable of unassisted catalytic hydrolysis of an unactivated amide bond. Documentation of rationally-designed catalytic antibody transformations of amide bonds have been limited to antibodies capable of activated amide hydrolysis (8), metallo-cofactor-assisted amide hydrolysis (20), and amide bond rearrangement (21). Also, naturally-occurring peptide hydrolysis by autoantibodies have been reported (22). It should be pointed out that in the last example the reported antibody activities were discovered rather than designed. Here we describe the first successful design of a catalytic antibody capable of unassisted hydrolysis of an unactivated amide bond.

In nature, the most commonly encountered amide bonds are found in peptides and proteins. Three principle types of amide bonds are found in peptide and proteins: as peptide bonds linking individual amino acids, in asparagine and glutamine amino acid side chains, and at the C-terminus of some peptides (i.e. C-terminal carboxamide). Hydrolyses of both types of amide bonds, peptide bonds and primary amide bonds (asparagine, glutamine and C-terminal amides), have the same or very similar Gibbs free energies of activation (23–25). Hence, they require the same amount of transition state stabilization to be catalyzed with similar rate enhancements.

Amidated peptide hormones that are important in disease states include: calcitonin (29), calcitonin gene-related peptide (30,31), big gastrin (32,33), and bombesin-like peptides [BLP, otherwise known as bombesin-related peptides (BRP) or gastrin-releasing peptides (GRP)] (34,35). Elevated calcitonin levels have been associated with several disease states including medullary thyroid carcinoma, C-cell hyperplasia, chronic renal failure, pancreatitis, mineral and bone disorders, and hyperthyroidism (29). Elevated gastrin is associated with gastrinomas, BLP with small cell lung cancer (SCLC) (33). Experimental treatments are underway to neutralize the effects of these hormones in disease states using monoclonal antibodies (anti-BLP)(36), neutral endopeptidase 24.11 (BLP hydrolysis)(37), and synthetic antagonists (BLP)(38–41).

Also of potential therapeutic relevance are peptides and proteins containing amino acids with amide side chains (e.g., asparagine and glutamine). Administration of bacterial asparaginase, which hydrolyzes the side chain carboxamide of free asparagine, has been shown to be an effective anti-leukemia agent (42).

U.S. patent application Ser. No. 190,271 of which this application is a continuation-in-part, describes analogs of peptide bonds and methods for eliciting catalytic antibodies which hydrolyze such peptide bonds. The analogs and antibodies described therein are directed towards the modification of peptide bonds which are secondary amide bonds whereas the present application is related to modification of primary amide bonds.

U.S. patent application Ser. No. 08/007,684 which is a continuation-in-part of International Application WO Serial No. 92/01047 (PCT/GB91/01134) describes the isolation and production of catalytic antibodies displayed on bacteriphage and the isolation and production of human catalytic antibodies. The disclosures of both of these applications are hereby incorporated herein by reference.

Based on the observations described above, it is desired to develop transition state analogs of primary amides to elicit catalytic antibodies which can cleave primary amide bonds in peptides and proteins.

It is desired to employ catalytic antibodies which catalyze the hydrolysis or formation of primary amide bonds as therapeutic agents by administration to living organisms. Modification of primary amide bonds in target peptides and proteins would expectedly alter their physiological function and therefore provide beneficial therapeutic effect on the living organisms.

SUMMARY OF THE INVENTION

The invention herein described provides methods for the production of catalytic antibodies which can hydrolyze primary amide bonds. Such antibodies can be directed to hydrolyze and/or form primary amide bonds specifically in selected peptides and other molecules. A direct result of this invention is the production of many different therapeutic products having benefit to the public which could not be developed based on the prior art.

It has surprisingly been found that compounds of this invention elicit antibodies which enhance the rate of hydrolysis (cleavage) or formation of primary amide bonds and, that such catalytic antibodies have therapeutic and industrial utility.

The present invention accordingly provides a compound of formula (I):

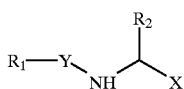
(I)

wherein:

Y is a polypeptide, $R_1$ is bonded to the N-terminus of Y and is hydrogen or a branched or linear, substituted or unsubstituted, $C_{1-21}$ alkyl, alkene, or alkyne group, $R_2$ is a side chain of a naturally occuring amino acid, and X is

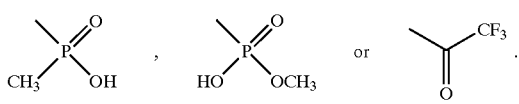

The present invention further provides for a compound of formula (I) wherein the polypeptide, Y, consists of the polypeptide sequence of a protein containing a C-terminal carboxamide with the C-terminal amino acid is omitted.

Also contemplated by the present invention are compounds of formula (i) wherein $R_1$ comprises a reactive group such as

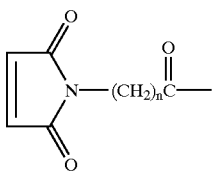

where n is an integer of 1 to 21, attached to the N-terminal amino acid of the polypeptide such that the comound of formula (I) can be chemically reacted with and attached to a carrier molecule.

Accordingly, immunogens are contemplated by the present invention wherein the compounds of formula (I) are attached to a carrier molecule.

The present invention also provides a compound of formula (II):

$$R-Y-[(CH_2)_n-X]_m \quad (II)$$

where in:

R is hydrogen or a branched or linear, substituted or unsubstituted, $C_{1-21}$ alkyl, alkene, or alkyne group, Y is a polypeptide, the $-(CH_2)_n-X$ groups replace side chains of asparagine or glutamine of said polypeptide, n is 1 or 2, m is an integer greater than or equal to one and less than or equal to the total number of asparagine and glutamine amino acids in said polypeptide, and X is

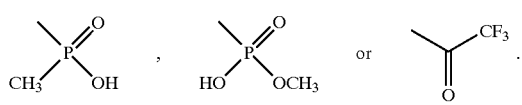

Also contemplated by the present invention are compounds of formula (ii) wherein $R_1$ comprises a reactive group such as

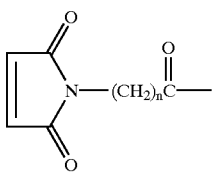

where n is an integer of 1 to 21, attached to the polypeptide such that the compound of formula (ii) can be chemically reacted with and attached to a carrier molecule.

Accordingly, immunogens are contemplated by the present invention wherein the compounds of formula (ii) are attached to a carrier molecule.

The present invention also provides for compounds of the formula (I) or (II) in which the peptide consists of 1 to 20 naturally occuring amino acids.

The present invention further provides a compound of the formula (III):

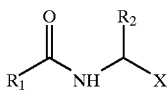

(III)

wherein:
R$_1$ is a branched or linear, substituted or unsubstituted, C$_{1-21}$ alkyl, alkene, or alkyne group,
R$_2$ is a side chain of a naturally occuring amino acid, and X is

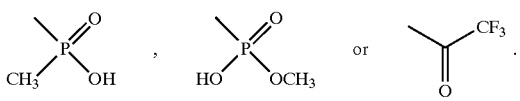

Also contemplated by the present invention are compounds of formula (III) wherein R$_1$ comprises a reactive moiety such as

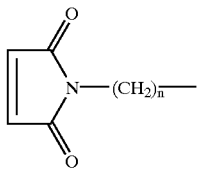

where n is an integer of 1 to 21, such that the comound of formula (III) can be chemically reacted with and attached to a carrier molecule.

Accordingly, immunogens are contemplated by the present invention wherein the compounds of formula (III) are attached to carrier molecules.

The present invention further contemplates antibodies which are capable of enhancing the rate of hydrolysis and/or the rate of formation of a primary amide bond.

Also contemplated are antibodies which are capable of enhancing the rate of hydrolysis and/or the rate of formation of a primary amide bond produced by the method comprising the steps of:
  (i) generating a gene library of antibody-derived domains;
  (ii) inserting coding for said domains into a phage expression vector; and
  (iii) isolating said catalytic antibodies.

Further contemplated are antibodies which are capable of enhancing the rate of hydrolysis and/or the rate of formation of a primary amide bond produced by the method comprising the steps of:
  (i) immunizing an animal with a composition comprising an analog of a reactant, reaction intermediate, or product of the hydrolysis reaction;
  (ii) removing antibody-producing lymphocytes from said animal; and,
  (iii) fusing the lymphocytes with myeloma cells and thereby producing hybridoma cells producing the antibody.

Also contemplated are antibodies which are capable of enhancing the rate of hydrolysis and/or the rate of formation of a primary amide bond obtained by the method comprising:
  (i) raising antibodies against a hapten
  (ii) immobilizing said antibodies
  (iii) adding a substrate to said antibodies, and
  (iv) identifying antibodies capable of catalyzing the conversion of said substrate to a product.

Further contemplated are antibodies obtained by the above method further comprising, after step (i):
  (i) concentrating said antibodies and
  (ii) purifying said antibodies.

Also provided by the present invention are methods for providing therapy in an animal or individual in need of said therapy comprising administering to said individual or animal an antibody capable of enhancing the rate of hydrolysis and/or formation of a primary amide bond. The animal or individual can be a patient.

BRIEF DESCRIPTION OF THE DRAWINGS

The following Detailed Description of the Invention will be better understood with reference to the accompanying Figures. wherein.

DETAILED DESCRIPTION OF THE INVENTION

Figure 1:
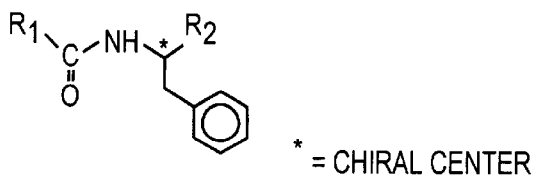
FIG. 1 shows the chemical structures of molecules used as haptens and inhibitors used for elicitation, screening and selection, and characterization of catalytic antibodies.

For the sake of clarity and convenience, the following definitions will be used in describing the invention:

An antibody-derived domain refers to a peptide sequence or multiple individual peptide sequences which are physically or chemically associated with one another derived from an antibody molecule. Single-chain antibodies and single chain domains of antibodies are included in the meaning of antibody-derived domain.

Throughout the application the term antibody is used in a generic sense and is meant to include antibody-derived domains.

An amino acid consists of a tetrahedral carbon atom to which is bonded an amino group, a carboxyl group, a hydrogen atom, and a distinctive group referred to as a "side chain." Naturally occuring amino acids are those amino acids that are synthesized by living organisms and can be polymerized via condensation to form peptides and proteins. Examples include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, 4-hydroxyproline, 5-hydroxylysine, epsilon-N-methyllysine, 3-methyl histidine, beta-alanine, gamma-aminobutyric acid, homocystein, homoserine, citrulline, ornithine, canavanine, djenkolic acid, and beta-cyanoalanine.

The C-terminus of a protein or peptide is the end of a linear polymer of amino acids in which the ultimate amino acid is bonded to the polymer by an amide bond via its amino group.

The N-terminus of a protein or peptide is the end of a linear polymer of amino acids in which the ultimate amino acid is bonded to the polymer by an amide bond via its carboxylic acid group.

A C-terminal carboxamide is a derivative of the ultimate amino acid on the C-terminal carboxylic acid of a peptide of protein in which the —OH of the carboxylic acid is replaced by —NH$_2$.

A primary amide bond is an amide bond in which the amide nitrogen is covalently bonded to two hydrogen atoms at neutral pH.

Peptide as used herein includes dipeptides and polypeptides.

A carrier molecule used in immunization with haptens is a molecule of high molecular weight (>10,000 daltons) to which a small molecule (hapten) can be covalently attached to cause the small molecule to become more immunogenic to an organism. Examples of carriers are keyhole limpet hemocyanin (KLH) and bovine serum albumin (BSA).

A polypeptide sequence of a peptide containing a C-terminal carboxamide with the C-terminal amino acid omitted means the amino acid sequence of a protein or peptide which normally contains a C-terminal carboxamide in which the ultimate C-terminal amino acid is removed by hydrolysis of the ultimate peptide bond or is omitted and is replaced by an —OH group.

The compounds of the present invention can contain alkyl, alkene, or alkyne groups which are substituted or unsubstituted. The term "substituted" means that one or more carbon or hydrogen atom is replaced by a substituent. Examples of suitable substituents, but to which the invention is not limited, include —OH, alkyl, chloro, fluoro, bromo, iodo, —NH$_2$, —NH(OH), —NH—NH$_2$, —N=NH, —NO$_2$, —OP(O)(OH)$_2$, —P(O)(OH)$_2$, —SO$_3$H, —SO$_2$H, aryl, —SH, —S—, —C(O)OH, —C(O)H, amide groups, ester groups, ether groups, alkenyl, alkynyl, —C(O)—, cyano, epoxide groups, and heterocyclic groups.

The invention disclosed herein entails the production of catalytic antibodies which are capable of catalyzing the hydrolysis or formation of primary amide bonds. Such primary amide bonds are found naturally in peptides and proteins such as in the side chains of asparagine and glutamine amino acids and occasionally at the carboxy terminus. Many naturally occuring peptides and proteins having various physiological functions are known to contain such primary amide bonds. The administration of catalytic antibodies which are capable of modifying such primary amide bonds as therapeutic agents alter physiological function of the peptides and proteins and provide therapeutic benefit to the subject.

Accordingly, the first successful design of a catalytic antibody capable of unassisted hydrolysis of an unactivated amide bond is described herein.

The catalytic antibodies of the present invention can be employed in either the hydrolysis of primary amide bonds or the formation of a primary amide bonds. Because any chemical reaction is reversible, a catalyst (e.g., a catalytic antibody) which catalyzes the reaction in one direction will also catalyze the reaction in the opposite derection. A catalyst does not alter the final equilibrium concentrations when included in a reaction medium, it only alters the rate at which equilibrium conditions are reached. Hence, the direction (forward or reverse reaction) in which a catalytic antibody (or other catalyst) enhances the reaction is dependent upon the concentrations of the reactants and products and the reaction conditions. A catalytic antibody prepared with a "forward" reaction as its intended catalytic function is equally able to catalyze the same reaction in the "reverse" direction.

The invention is exemplified by the design of haptens that elicit antibodies capable of the hydrolysis of C-terminal amide bonds. Antibodies with such activities have therapeutic and industrial applications. A number of peptide hormones terminate in biologically active carboxamide groups whose hydrolysis is valuable in treatments of various diseases (Table 1) (26–28). One of many additional therapeutic targets are antibodies that hydrolyze the asparagine or glutamine side-chain in peptides. In addition, as described below, catalytic antibodies are useful in the industrial synthesis of amidated peptides of therapeutic value.

TABLE I

Selected Naturally-Occurring Bioactive α-Amidated Peptides (26–28)

| α-Amidated (C-terminal) Residue | Peptide |
|---|---|
| A alanine | b,o CRH; μ-Conotoxin |
| C cysteine | crustacean cardioactive peptide; conotoxins G1, M1, S1 |
| D aspartic acid | deltorphin |
| E glutamic acid | joining peptide; melittin (bee). |
| F phenylalanine | FMRF-NH$_2$; gastrin; cholecystokinin; CGRP; γ$_1$MSH |
| G glycine | oxytocin; vasopressin; GnRH; pancreastatin; leucokinin I, II; Manduca adipokinetic hormone; lutropin releasing hormone |
| H histidine | apamin (bee); scorpion toxin II |
| I Isoleucine | h, r CRH; PHI; Manduca diuretic hormone; rat neuropeptide EI (melanin concentrating hormone) |
| K lysine | cecropin A; PACAP38 (pituitary adenylate cyclase activating peptide 38); conotoxin GiA; egg laying hormone (snail); tertiapin (bee) |
| L leucine | b, h GHRH; β-amidorphin; mastoparan; cecropin B; buccalin; myomodulin; PACAP27; proglucagon (111–123) |
| M methionine | Substance P; Substance K; PHM; gastrin releasing peptide; neurokinin A, B; neuromedin B, C; bombesin (frog) |
| N asparagine | VIP (mammalian); neuromedin U; corazonin; mast cell degranulating peptide |
| P proline | calcitonin; Thyrotropin releasing hormone |
| Q glutamine | melittin; levitide |
| R arginine | preproglucagon (111–123); short insectotoxin (scorpion) |
| S serine | frog granuliberin-R; cecropin B (moth); dermorphin (frog) |
| T threonine | rat galanin; avian VIP; locust adipokinetic hormone |
| V valine | αMSH; r, p, h secretin; metorphamide/adrenorphin; urotensin I (fish) |
| W tryptophan | cockroach myoactive peptide; sea anemone peptide; crustacean erythrophore concentrating peptide |
| Y tyrosine | Neuropeptide Y; PYY; PP; ω-conotoxin; amylin |

SCLC is a particularly attractive therapeutic target for de-amidating antibodies. A great majority of patients with SCLC die despite current conventional chemotherapeutic regimens (34). SCLC has been shown to have "neuroendocrine" properties associated with it (34,43,44). SCLC cells release a number of C-terminally-amitated peptide growth factor hormones. As shown in Table 11, SCLC cells not only produce the peptide hormones but also receptors for the hormones (34). Thus, SCLC tumors probably accelerate their own growth by an autocrine mechanism (43). A catalytic antibody capable of de-amidating one or more of these peptides, or preferably a battery of different catalytic antibodies each capable of de-amidating a different peptide expressed by SCLC cells, can have therapeutically value. Such catalytic antibodies can be especially effective if directed to a tumor site by being conjugated to a tumor-binding agent such as a tumor antigen-binding monoclonal antibody (45).

TABLE II

Hormones Produced and Receptors Expressed by Human SCLC (34)

| Hormone Name | Produced by SCLC | Receptor Expressed by SCLC |
|---|---|---|
| GRP | + (Met-NH$_2$ terminus) | + |
| IGF-1 | + (Pro-NH$_2$ terminus) | + |
| Transferrin | + | + |
| Calcitonin | + | + |
| AVP | + (Gly-NH$_2$ terminus) | + |
| Opioid Peptides | + | + |
| Neurotensin | + | + |
| Glucagon | + | ? |
| Substance P | + (Met-NH$_2$ terminus) | ? |
| Somatostatin | + | ? |
| CCK | − (Phe-NH$_2$ terminus) | + |
| TGFα | + | + |
| VIP | − (Asn-NH$_2$ terminus) | + |
| ACTH | + | ? |
| GGAP | + | + |
| ANF | + | ? |
| Galanin | ? (Ala-NH$_2$ terminus (Porcine), Thr-NH$_2$ terminus (Rat), unknown for Human) | + |
| Bradykinin | ? | + |
| Interferon-γ | ? | + |
| GM-CSF | ? | + |
| Neurokinin A | + (Met-NH$_2$ terminus) | + |
| Neurokinin B | + (Met-NH$_2$ terminus) | + |

In industrial synthesis, there is a need for new methods for producing amidated peptides (46–50). Peptides such as growth-hormone-releasing factor (48), calcitonin (49,50), calcitonin gene related peptide (30), and neurokinin A (51, 52) have therapeutic value and tailor-made catalytic synthetic methods are extremely useful. Methods under investigation are the use of recombinant rat α-amidating enzyme (48,49) and yeast carboxypeptidase Y (50). Catalytic antibodies capable of amide hydrolysis can be used industrially for preparation of C-terminal peptide amides. Peptide hydrolysis is thermodynamically a reversible reaction and accordingly can be made to go in the opposite (synthetic) direction. The back reaction is facilitated by using anhydrous organic or organic/aqueous solvents. There is a large body of literature on using organic solvents to encourage enzymic reactions that are thermodynamically unfavorable in water (53,54). This literature includes a study demonstrating the retention of antibody-antigen binding in organic solvents (55). Indeed, in other work a catalytic antibody has been shown to function catalytically in organic solvents (56). Amide synthesis using catalytic antibodies in a transesterification reaction has been reported (57,58), but a specific binding site for the incoming primary amine reactant is required in that work. Because primary amide synthesis using that method would be extremely difficult since it would require the design of an antibody with a specific binding site for ammonium hydroxide, a very small molecule.

Antibodies to formula (I), (II) and (III) compounds can be administered in any suitable form which is effective, for instance, orally, intravenously, subcutaneously, intradermally, intratumorally, and the like. Antibodies to formula (I), (II) and (III) compounds can be administered in any suitable carrier, such as saline. These formulations can be coadministered with other treatments; for instance, antibodies to formula (I), (II) and (III) compounds can be administered with antibiotics. Furthermore, the antibodies to formula (I), (II) and (III) compounds can be administered as a mixture with other antibodies, for instance with antibodies to other formula (I), (II) or (III) compounds., i.e., the antibodies of the present invention can be administered as a "cocktail." This cocktail can include both IgG and IgM antibodies as well as both binding and catalytic antibodies. The term "antibodies," is meant to included either binding or catalytically active fragments of antibodies and/or also includes single-chain antibodies and single-chain fragments of antibodies.

In addition, the invention contemplates that the antibodies to formula (I), (II) and (III) compounds can be dispensed in concentrated form or lyophilized form for dilution by the ultimate user. These preparations can be in kit form. The kit form can also include suitable instructions for administration in accordance with this invention.

The following non-limiting Examples are given by way of illustration only and are not to be considered a limitation of the invention.

SYNTHESIS AND PREPARATION OF HAPTEN, INHIBITOR, AND SUBSTRATE COMPOUNDS

Figure 2:
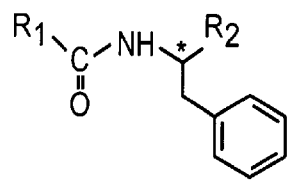
FIG. 2 shows the chemical structures of molecules used as substrates used for screening and selection as well as in characterization of catalytic antibodies.
Figure 3:
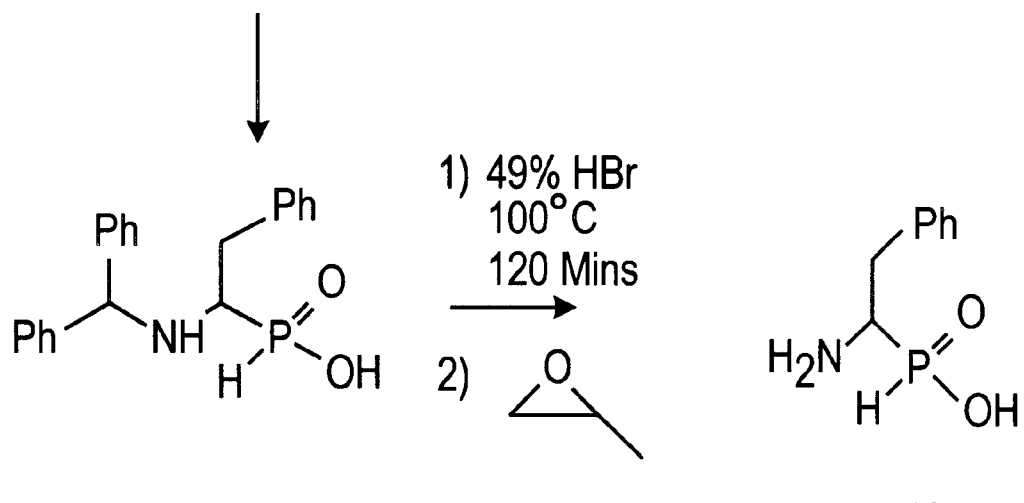
FIGS. 3–10, and 12 show reaction schemes for the synthesis of haptens, inhibitors, and substrates used in the elicitation, screening and selection, and characterization of catalytic antibodies.

The synthesis of the compounds depicted in FIGS. 1 and 2 was achieved according to the schemes depicted in FIGS. 3–10 accompanying this description.

It should be noted that, whereas some synthetic methods and compounds are specific as to a particular stereochemistry, this is not meant in any way to exclude methods and compounds of different stereochemistry or of a mixture of stereochemistries (or stereoisomers).

The compounds depicted in FIG. 1, used herein as haptens and inhibitors, all include tetrahedral atoms as analogs of the transition state at the position of the carbonyl carbon atom of the primary amide bond. Compounds 1–6 all include phosphorous as this tetrahedral atom whereas the tetrahedral geometry in compounds 7 and 8 is provided by hydration of the trifluoroketone. Such trifluoroketones are known to exist in equilibrium with their hydrated tetrahedral form (Begue et al., Tetrahedron, Vol. 47 (1991); 3207–3258):

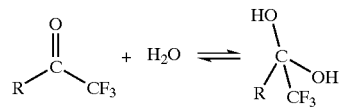

The equilibrium under aqueous conditions is known to exist far to the right, i.e., most of the compound exists in the hydrated form. Hence, trifluoroketones can act as tetrahedral transition state analogs for hydrolysis of ester and amide bonds.

The synthesis of the compounds in FIGS. 1 and 2 generally followed the following description:

The synthesis of the (±) 1-Amino-2-phenylethyl phosphonous acid (19, FIG. 3) was essentially carried out as described by E. Baylis et al., J. Chem. Soc. Perkin Trans 1,12, (1984):2845–2853.

Figure 4:
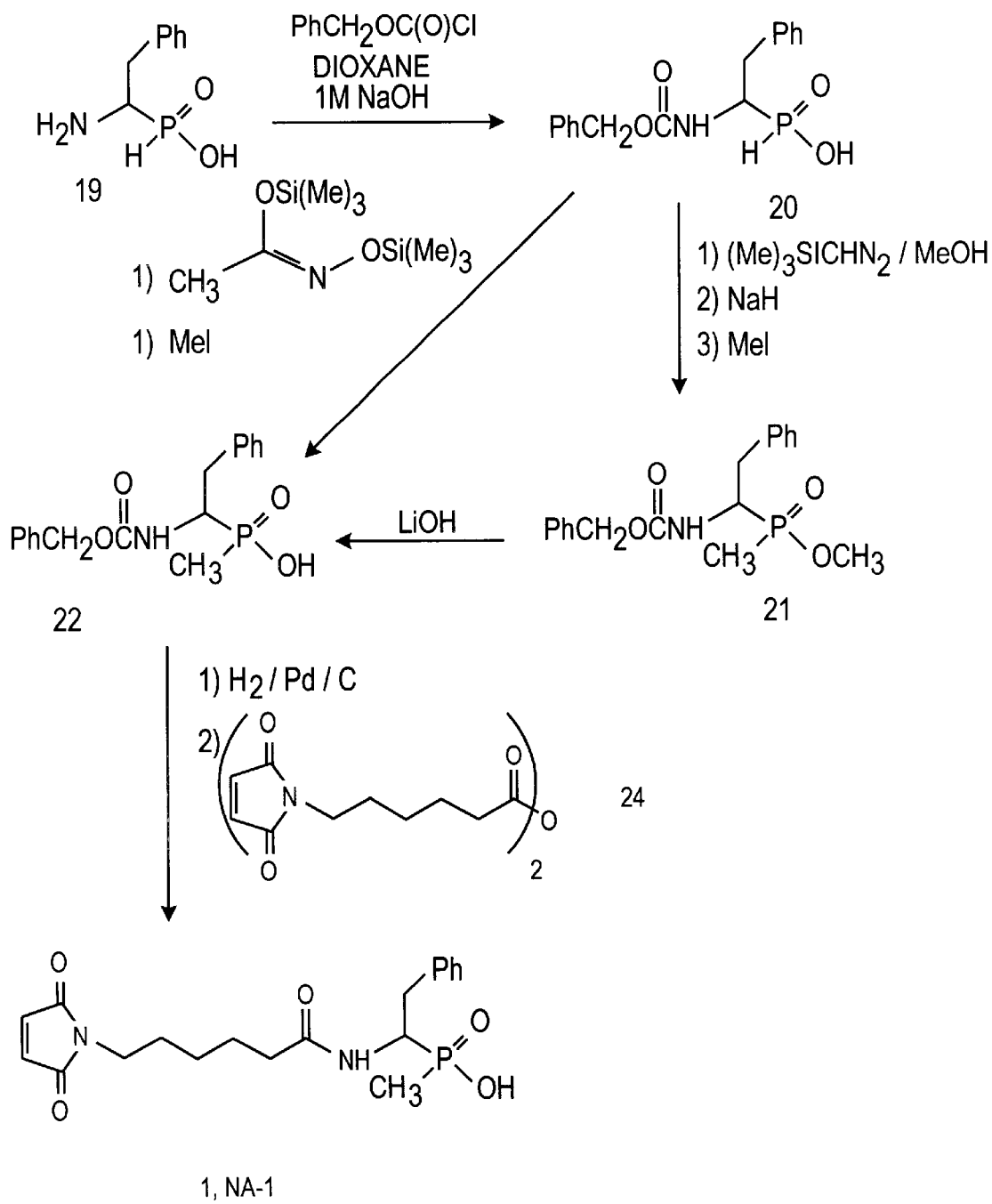
Figure 5:
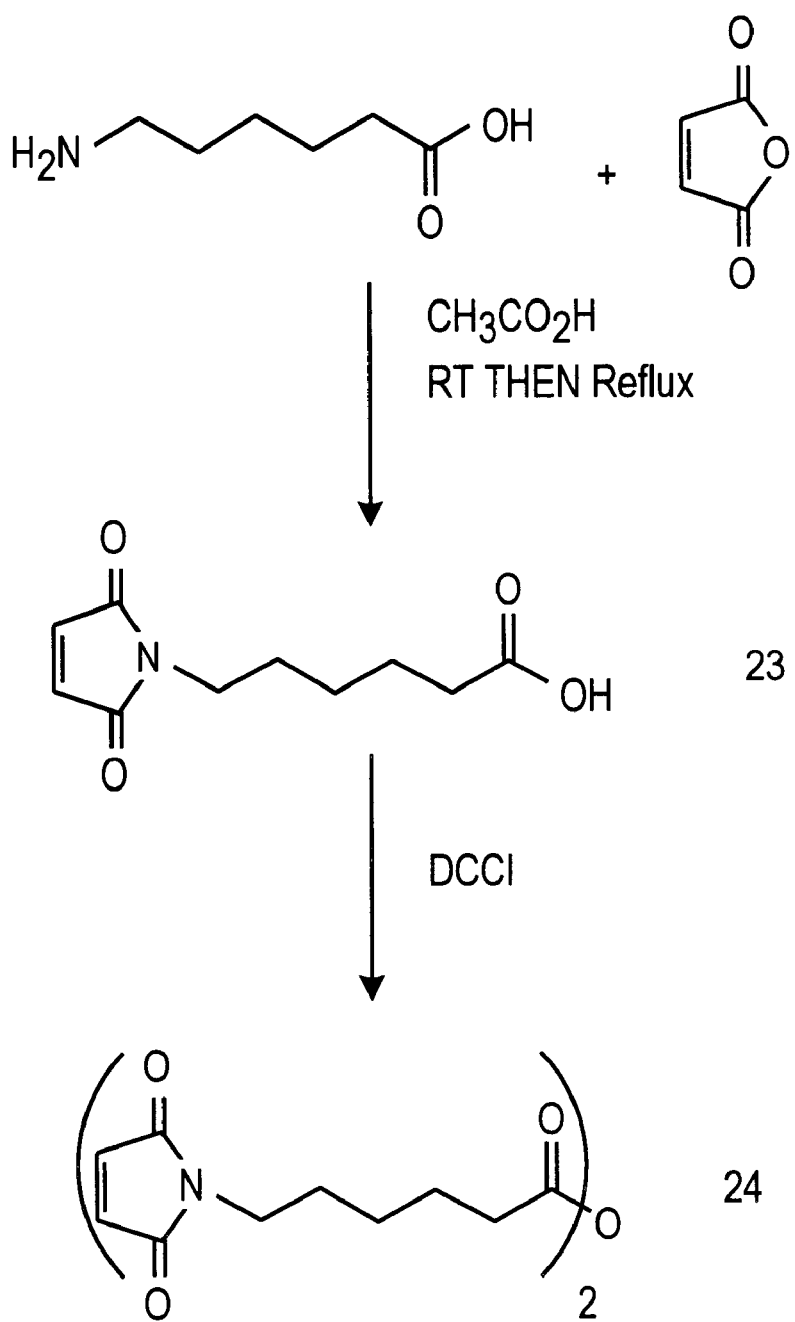

The NA-1 hapten was prepared as outlined in FIG. 4. (±) 1-Amino-2-phenylethyl phosphonous acid (19) was amino protected using benzyl chloroformate to give (±) N-CBZ-1-amino-2-phenylethyl phosphonous acid (20). Compound 20 was converted to Compound 22 by a direct method that uses N,O-Bis(trimethylsilyl)acetamide and methyl iodide. This reaction can be unpredictable so an alternate more reliable method was found. Compound 20 was first O-methylated with trimethylsilyldiazomethane followed by methanol and then P-methylated using sodium hydride and methyl iodide to give Compound 21. Hydrolysis of Compound 21 with lithium hydroxide afforded the same intermediate, Compound 22 (FIG. 4). Removal of the CBZ group from Compound 22 by catalytic hydrogenation and subsequent acylation by the symmetrical anhydride of 6-Maleimidocaproic acid (24) yielded the final NA-1 hapten (1).

The symmetrical anhydride of 6-Maleimidocaproic acid (Compound 24, FIG. 5) was prepared by the reaction of maleic anhydride and e-Amino-n-caproic acid in the presence of acetic acid to give 6-Maleimidocaproic acid (Compound 23) which was then converted to Compound 24 using dicyclohexyl carbodiimide (DCCl).

The synthesis of (±)diphenyl 1-(N-Benzyloxycarbonyl)-amino-2-phenylethyl phosphonate 25 (FIG. 6) followed the procedure reported by J. Oleksyszyn et al., *Synthesis* (1 979):985–986. The preparation of the methylphosphonate 26 (FIG. 6) was adapted from the paper by Y. Vo-Quang et al., *Tetrahedron Letters*, Vol. 28, (1987):6167–6170. Removal of the CBZ group from Compound 26 by catalytic hydrogenation and subsequent acylation by the symmetrical anhydride of 6-Maleimidocaproic acid (24) yielded the final RT-2 hapten (3, RT-2).

The synthesis of the β-amino trifluoroalcohol hydrochloride 28 (FIG. 7) through intermediate 27 followed the procedure described by B. Imperiali and R. H. Abeles, *Tetrahedron Letters*, Vol. 27 (1986):135–138. Acylation of Compound 28 with the symmetrical anhydride of 6-Maleimidocaproic acid (24) afforded the alcohol Compound 29, which on oxidation with Dess-Martin Oxidant yielded the final WH-2 hapten (8).

Figure 8:
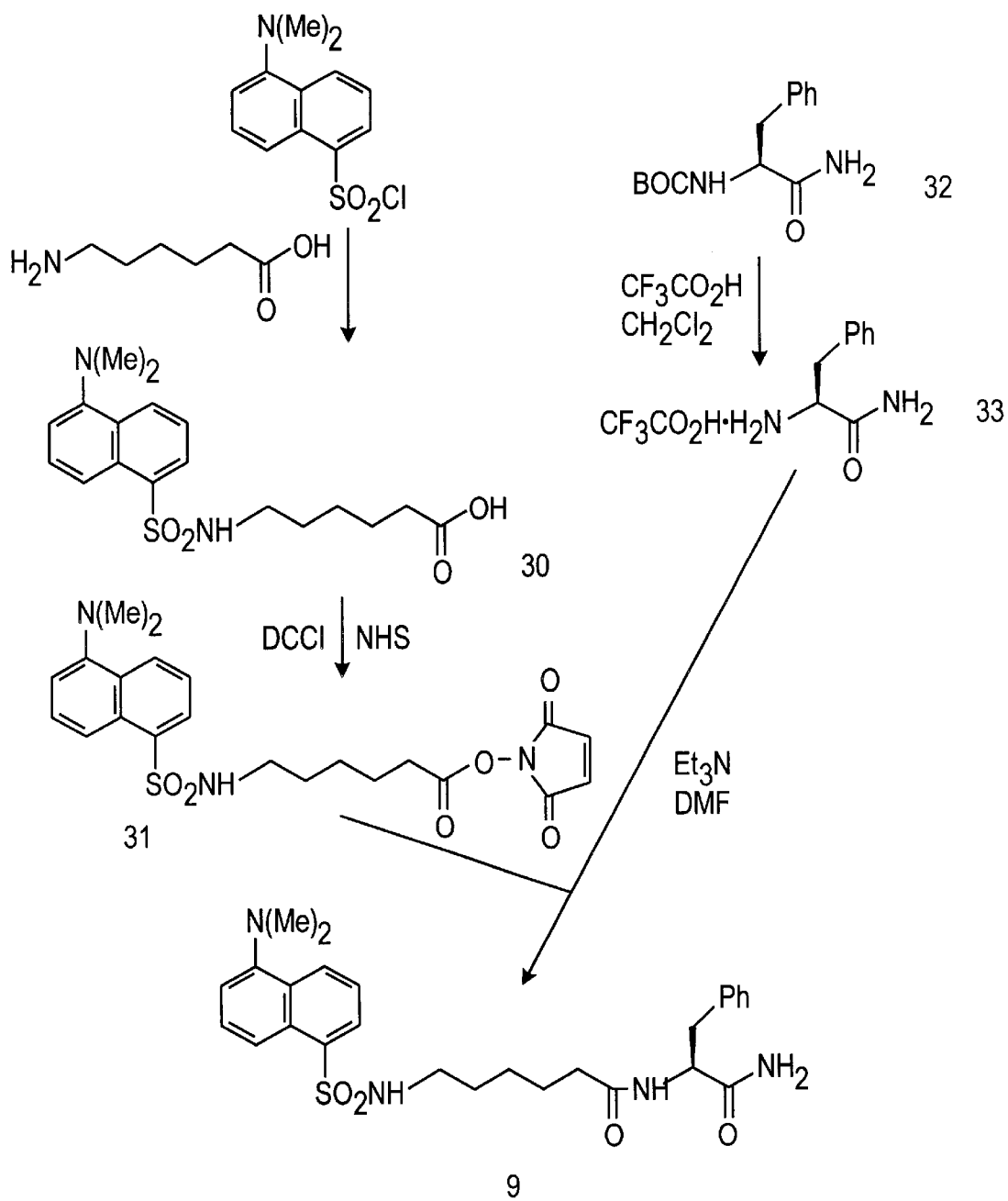
Figure 9:
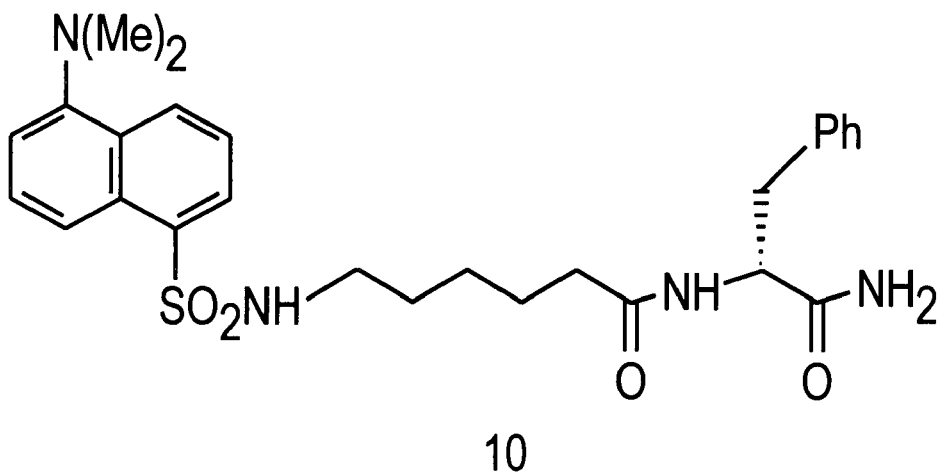
Figure 9:
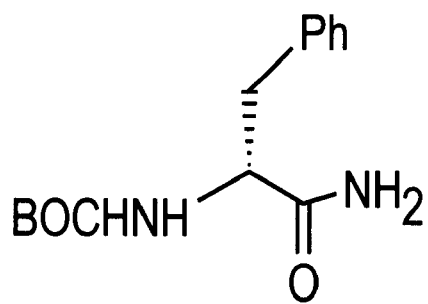
Figure 10:
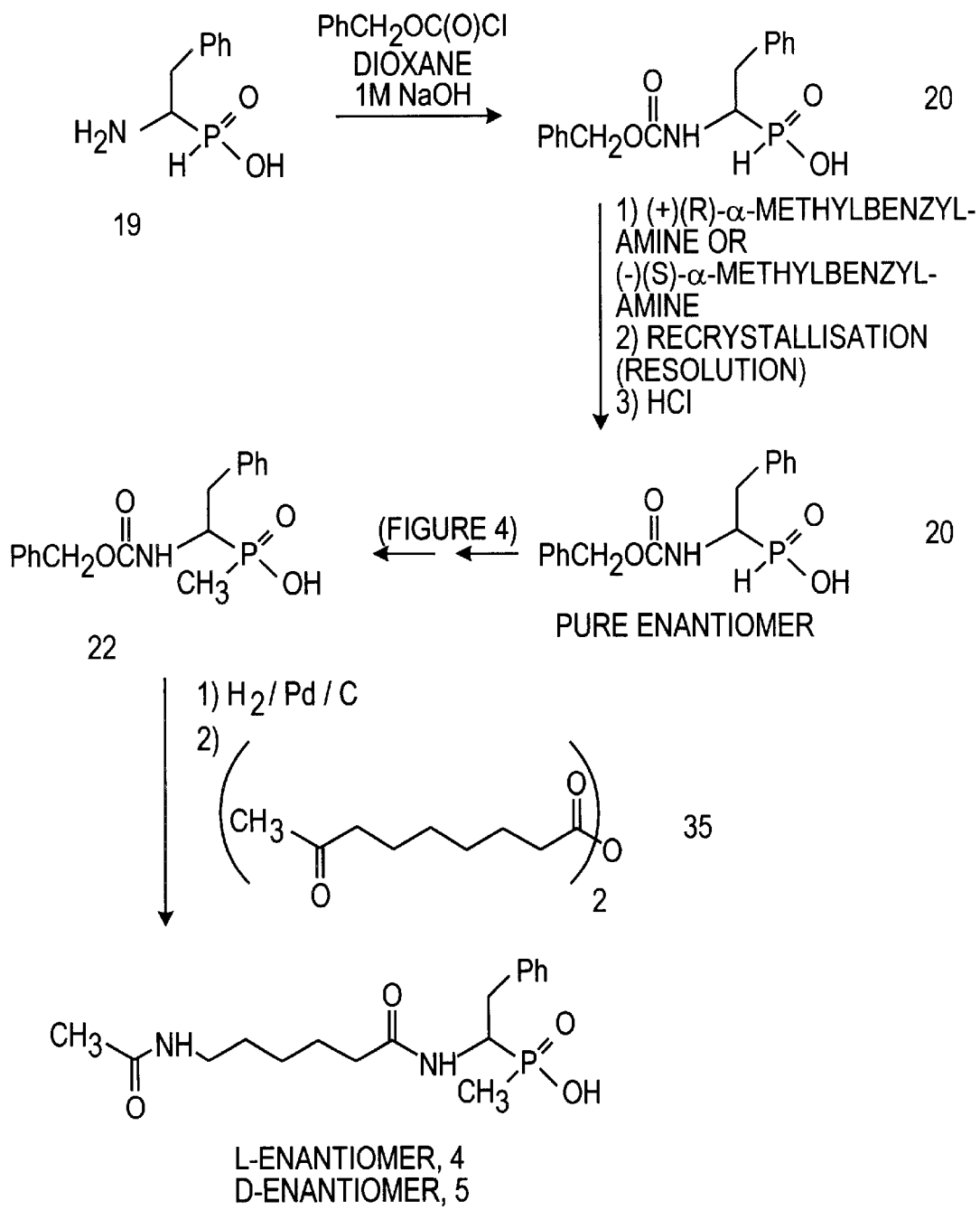

Dansylated-ε-amino-n-caproic acid (30, FIG. 8) was prepared from the coupling of dansyl chloride and e-Amino-n-caproic acid. Activation of Compound 30 with DCCl and N-Hydroxysuccinimide yielded Compound 31. The preparation of BOC-L-Phe-NH$_2$ (32, FIG. 8) followed the procedure reported by Shui-Tein Chen et al., *Synthesis*, Vol. 1 (1988):37–38. Deprotection of Compound 32 with trifluoroacetic acid gave Compound 33, which was then reacted with Compound 31 in the presence of triethylamine which gave the final product, Compound 9 (FIG. 8).

The synthesis of 10 (FIG. 9) followed the same set of reactions as for the synthesis of 9 (FIG. 8.) except that BOC-D-Phe-NH$_2$ (34, FIG. 9) was used instead of 32. Compound 34 was prepared by the procedure of Shui-Tein Chen et al., *Synthesis* (1988):37–38.

(±) 1-Amino-2-phenylethyl phosphonous acid (19) was resolved by first converting to its (±) N-benzyloxycarbonyl derivative (20, FIG. 10) and then recrystallizing its (+)(R)- and (−)(S)-α-methylbenzylamine salts as described by E. Baylis et al., *J. Chem. Soc. Perk. Trans I*, Vol. 12 (1984):2845–2853. After acidification, the pure enantiomers of Compound 20 were separately converted to the two enantiomers of Compound 22 by the same method as shown in FIG. 4. Removal of the CBZ group from Compound 22 by catalytic hydrogenation, and the subsequent acylation by the symmetrical anhydride of N-Acetyl-6-amino n caproic acid (35), yielded the purified enantiomers of NA-1-hapten (4 and 5, FIG. 10).

The synthesis of 6 (FIG. 1) followed the same chemical steps as for the synthesis of Compound 3 (FIG. 6) except that acetic anhydride was used instead of the symmetrical anhydride of 6-Maleimidocaproic acid (24). Similarly, the synthesis of 7 (FIG. 1) followed the same chemical steps as the synthesis of Compound 8 (FIG. 7) except that acetic anhydride was used instead of Compound 24.

Preparation of substituted or alkene or alkyne compounds within the definitions of formula (I), (II) and (III) was as presented below, except that the appropriate substituted or unsubstituted alkyl, alkene or alkyne precursor compound was substituted in the chemical synthesis. One of ordinary skill in the art can readily develop the necessary synthetic procedures based on the examples and description herein, without undue experimention.

EXAMPLE 1

Synthesis and Preparation of NA-1 Hapten, Compound 1

Synthesis of (±)N-CBZ-1-Amino-2-phenylethyl Phosphonous Acid (20)

To a solution of (±)1-Amino-2-phenylethyl phosphonous acid (19) (70 mmol) in dioxane (200 mL) and aqueous 1 M NaOH (75 mL) at 0° C. was added dropwise benzyl chloroformate (20 mL). The pH of the solution during this addition was kept at 8–9 with the simultaneous addition of aqueous 1M NaOH (75 mL). The reaction mixture was stirred at room temperature for a further 16 hours and then was concentrated in vacuo to half volume. Washed with diethyl ether (2×75 mL) and then acidified to pH1 with the addition of concentrated aqueous hydrochloric acid. Extracted with ethyl acetate (3×80 mL) and the combined organic phases were washed with water (1×20 mL), dried over anhydrous MgSO$_4$, filtered and evaporated in vacuo which gave (±)N-CBZ-1-amino-2-phenylethyl phosphonous acid (20) (15.44 g).

This was confirmed by spectroscopy—$^1$H NMR (CD$_3$OD) δ 2.78 (m, 1H), 3.15 (m, 1H), 3.97 (m, 1H), 4.90 (s, 2H), 4.96 (d, 1H), 6.95 (d, 1H, J=540 Hz), 7.25 (m, 5H).

Preparation of Compound 21

(±)N-CBZ-1-amino-2-phenylethyl phosphonous acid (20) (1.60 mmol) was dissolved in methanol (5 mL) and a solution of trimethylsilyldiazomethane (10% by weight in hexane) was added until the yellow color persisted. Glacial acetic acid was then added until the yellow color disappeared. The solution was evaporated in vacuo to dryness. The residue was redissolved in dry THF (2 mL) and the solution transferred to a suspension of sodium hydride (1.53 mmol) in THF (2 mL), which was cooled to 0° C. The reaction mixture was stirred at room temperature for 30 minutes and then iodomethane (2.25 mmol) was added. After a further 3 hours of stirring, the reaction was quenched by the addition of saturated aqueous NH$_4$Cl solution (35 mL) and extracted with ethyl acetate (75 mL). The organic phase was washed with water (5 mL), dried over anhydrous Na$_2$SO$_4$, filtered, concentrated in vacuo and chromatographed on silica gel using methanol:methylene chloride (8:92) which gave Compound 21 (0.190 g).

This was confirmed as a mixture of diastereomers by spectroscopy—$^1$H NMR (CDCl$_3$) δ 1.46 and 1.45 (2d, 3H), 2.85 (m, 1H), 3.30 (m, 1H), 3.70 and 3.78 (2d, 3H), 4.10 and 4.30 (2m, 1H), 4.95 and 5.07 (2d, 1H), 5.00 (s, 2H), 7.20 and 7.33 (2m, 5H).

Preparation of Compound 22

Compound 21 (0.530 mmol) was dissolved in dioxane (0.55 mL) and water (0.50 mL). To this solution was added aqueous 2M LiOH (0.55 mL) and the mixture was vigorously stirred at room temperature for 48 hours. Water (25 mL) was added and the aqueous solution was washed with ethyl acetate (1×25 mL), acidified to pH 0 with concentrated hydrochloric acid and the aqueous phase extracted with ethyl acetate (2×40 mL). The organic extracts were combined, dried over anhydrous $Na_2SO_4$, filtered and evaporated in vacuo to give Compound 22 (0.153 g).

This was confirmed by spectroscopy—$^1$H NMR ($CD_3OD$) δ 1.44 (d, 3H), 2.75 (m, 1H), 3.22 (m, 1H), 4.08 (m, 1H), 4.87 (s, 2H), 4.95 (d, 2H), 7.26 (m, 5H).

Preparation of Compound 1, NA-1

A mixture of 10% Pd-C (10% by weight, 30 mg) and Compound 22 (0.31 mmol) in methanol (30 mL) was stirred at room temperature under an atmosphere of hydrogen until the starting material was consumed as observed by thin layer chromatography (TLC) (4 hours). The catalyst was filtered out through a pad of celite, washed with methanol (20 mL) and water:methanol (1:9, 10 mL). All solvents were combined and evaporated in vacuo to give a solid (40 mg). The solid was dissolved in DMF (2 mL) and a solution of 6-Maleimidocaproic symmetrical anhydride (24) (0.20 mmol) in DMF (2 mL) was added followed by triethylamine (0.10 mL). The reaction was stirred for 16 hours and then quenched by the addition of aqueous 1M potassium phosphate pH6 (2 mL). The product, Compound 1 (12 mg) was isolated pure using reverse phase $C_{18}$ hplc. Buffer A was water, Buffer B was acetonitrile:water (95:5), flow rate 3.5 mL min$^{-1}$ and gradient was 2–30% Buffer B over 30 minutes.

This was confirmed by spectroscopy—$^1$H NMR ($D_2O$) δ 0.80 (m, 2H), 1.20 (d, 3H), 1.25 (m, 2H), 1.35 (m, 2H), 2.05 (m, 2H), 2.65 (m, 1H), 3.20 (m, 1H), 3.40 (t, 2H), 3.55 (d, 1H), 4.20 (m, 1H), 6.80 (s, 2H), 7.30 (m, 5H).

EXAMPLE 2

Synthesis and Preparation of Hapten RT-2, Compound 3

Preparation of 6-Maleimidocaproic Acid 23

A solution of maleic anhydride (0.05 mole) in acetic acid (20 mL) was mixed with a solution of ε-Amino-n-caproic acid (0.05 mole) in acetic acid (50 mL) and stirred at room temperature for 2 hours. An additional amount of acetic acid (150 mL) was added and the reaction mixture refluxed for 16 hours. The reaction mixture was evaporated under vacuo to an oil and chloroform was then added (50 mL). The solution was left to stand for 16 hours at room temperature whereupon impurities were precipitated out of the solution. The precipitate was filtered and the filtrate was collected, evaporated under vacuo and chromatographed on silica gel using chloroform:acetic acid (95:5) to give 6-Maleimidocaproic acid 23 (8 g).

This was confirmed by spectroscopy—$^1$H NMR ($CDCl_3$) δ 1.30 (m, 2H), 1.6 (m, 4H), 2.35 (t, 2H), 3.5 (t, 2H), 6.7 (s, 2H).

Preparation of Compound 24

6-Maleimidocaproic acid 23 (9.8 mmol) was dissolved in dry methylenechloride (10 mL) and DCCl (4.10 mmol) was added. After 3 hours stirring at room temperature, the reaction mixture was filtered and the filtrate was evaporated in vacuo to give Compound 24 (1.9 g).

Preparation of RT-2 Hapten (3)

A mixture of 10% Pd-C (10% by weight, 40 mg) and Methyl-N-CBZ-1-amino-2-phenylethyl phosphonous acid (26) (0.43 mmol) in methanol (5 mL) was stirred at room temperature under an atmosphere of hydrogen for 2 hours. The catalyst was filtered out through a pad of celite, washing with methanol:water (1:1, 20 mL) and all solvents were combined and evaporated in vacuo to give a solid (87 mg). This solid was divided into five portions of 13 mg. Each portion was treated separately by the addition of a solution of Compound 24 (0.12 mmol) in DMF (0.2 mL) followed by triethylamine (0.02 mL). The reaction mixture was vigorously stirred, and after 10 minutes, was quenched by the addition of aqueous 1M potassium phosphate pH 5.5 (0.20 mL). All the portions, after being quenched, were combined and the product, compound RT-2 Hapten (3) (60 mg), was isolated pure as its triethylammonium salt using reverse phase $C_{18}$ hplc. Buffer A was water, Buffer B was acetonitrile:water (95:5) flow rate 3.5 mL min$^{-1}$ and gradient was 1–60% Buffer B over 30 minutes. Product peak eluted with a retention time of 19 minutes.

This was confirmed by spectroscopy—$^1$H NMR ($D_2O$) δ 0.80 (m, 2H), 1.25 (t, 9H), 1.30 (m, 4H), 2.05 (t, 2H), 2.70 (m, 1H), 3.20 (m, 1H), 3.25 (q, 6H), 3.60 (d, 3H), 4.40 (m, 1H), 6.75 (s, 2H), 7.30 (m, 5H).

EXAMPLE 3

Synthesis and Preparation of Hapten WH-2, Compound 8

Preparation of Compound 29

β-Aminotrifluoroalcohol hydrochloride 28 (0.082 mmol) was dissolved in a mixture of aqueous 1M potassium phosphate pH6 (1 mL) and acetonitrile (2 mL). Compound 24 (0.164 mmol) was added and the reaction mixture was stirred for 16 hours at room temperature. The mixture was evaporated in vacuo to a solid, acetonitrile (2 mL) added and the supernatant was purified by reverse phase $C_{18}$ hplc to give Compound 29 (20 mg) as two peaks of retention times of 16.36 minutes and 16.58 minutes. Buffer A was aqueous 25mM Triethylammonium acetate pH 5.5, Buffer B was acetonitrile:water (95:5), flow rate 3 mL min$^{-1}$ and the gradient was 5–80% Buffer B over 35 minutes.

This was confirmed as a mixture of diastereomers by spectroscopy—$^1$H NMR ($CDCl_3$) δ 1.25 (m, 2H), 1.58 (m, 2H), 2.10 and 2.15 (2t, 2H), 2.96 (m, 1H), 3.07 (m, 1H), 3.50 (m, 2H), 3.92 and 4.15 (2m, 1H), 4.23 and 4.38 (2m, 1H), 5.85 and 6.38 (2d, 1H), 6.69 and 6.70 (2s, 2H), 7.30 (m, 5H).

Preparation of WH-2 Hapten (8)

Compound 29 (0.0485 mmol) was dissolved in $CH_2Cl_2$ (1 mL) and Dess-Martin Oxidant (0.179 mmol) was added. After 3 hours stirring at room temperature, the reaction mixture was evaporated in vacuo. A mixture of water (1 mL) and acetonitrile (2 mL) were added and after centrifugation, the supernatant was purified by reverse phase $C_{18}$ hplc to give WH-2 Hapten (8) (10 mg) as a single peak of retention time of 15.33 minutes. Buffer A was aqueous 25mM Triethylammonium acetate pH 5.5, Buffer B was acetonitrile:water (95:5), flow rate 3 mL min$^{-1}$ and the gradient was 5–80% Buffer B over 35 minutes.

EXAMPLE 4

Synthesis and Preparation of Substrate Compound 9

Preparation of Dansylated-ε-Amino-n-caproic Acid (30)

To a solution of ε-amino-n-caproic acid (12.7 mmol) and triethylamine (70 mmol) in methanol (35 mL) was added dansyl chloride (11.48 mmol). After 2 hours stirring at room temperature, the reaction mixture was evaporated in vacuo. Aqueous 1M NaOH (100 mL) was added and the mixture was washed with diethyl ether (2×75 mL). The aqueous phase was acidified to pH 2–3 with concentrated hydrochloric acid and extracted with chloroform (2×100 mL). The organic phases were combined, dried over anhydrous $Na_2SO_4$, filtered and evaporated in vacuo to give Compound 30 (2.6 g).

This was confirmed by spectroscopy—$^1$H NMR ($CDCl_3$) δ 1.20 (m, 2H), 1.40 (m, 4H), 2.20 (t, 2H), 2.95 (m, 2H), 3.00 (s, 6H), 4.90 (t, 1H), 7.60 (m, 3H), 8.25 (d, 1H), 8.40 (d, 1H), 8.65 (d, 1H).

Preparation of Compound 33

BOC-L-Phe-$NH_2$ (32) (1 mmol) was dissolved in methylene chloride (6 mL) and trifluoroacetic acid (2 mL) was added. After 90 minutes stirring at room temperature, the reaction mixture was evaporated in vacuo. Methylene chloride (1 mL) was added and this solution was dropwise added to stirred diethyl ether (100 mL). The resultant precipitate was collected and washed with more diethyl ether (5 mL). Dried the precipitate under vacuo to give Compound 33 (0.240 g).

This was confirmed by spectroscopy—$^1$H NMR ($D_2O$) δ 3.20 (m, 2H), 4.30 (m, 1H), 7.40 (m, 5H).

Preparation of Compound 9

Compound 30 (0.65 mmol) and N-hydroxysuccinimide (0.65 mmol) were dissolved in methylene chloride (2 mL) and DCCl (0.65 mmol) was added. After 5 hours stirring at room temperature, the reaction mixture was filtered and the filtrate was concentrated to a solid (31). The solid was dissolved in DMF (2 mL) and Compound 33 (0.54 mmol) was added followed by triethylamine (1.30 mmol). The reaction mixture was stirred at room temperature for 16 hours and the mixtrue was then evaporated in vacuo to a solid. The solid was dissolved in methylene chloride (2 mL) and chromatographed on silica gel using methanol:methylene chloride (5:95) which gave Compound 9 (0.230 g).

This was confirmed by spectroscopy—$^1$H NMR ($CDCl_3$) δ 1.20 (m, 2H), 1.40 (m, 4H), 2.10 (t, 2H), 3.85 (m, 2H), 3.90 (s, 6H), 4.70 (q, 1H), 5.40 (t, 1H), 5.60 (bs, 1H), 6.00 (bs, 1H), 6.35 (d, 1H), 7.25 (m, 5H), 7.60 (m, 3H), 8.25 (d, 1H), 8.35 (d, 1H), 8.60 (d, 1H).

EXAMPLE 5

Synthesis and Preparation of Inhibitor Compounds 4 and 5

A mixture of 10% Pd-C (10% by weight, 100 mg) and Compound 22 (0.683 mmol) resolved by using (+)(R)-α-methylbenzylamine) in methanol (10 mL) was stirred at room temperature under an atmosphere of hydrogen for 3 hours. The catalyst was filtered out through a pad of celite, washed with methanol (10 mL) and water:methanol (1:9, 5 mL). All solvents were combined and evaporated in vacuo to a solid.

In a separate flask, 6-N-Acetyl n caproic acid (4.05 mmol) was dissolved in a mixture of methylenechloride (25 mL) and DMF (3 mL). To this solution was added DCCl (2 mmol) in methylenechloride (10 mL). After one hour stirring at room temperature, the reaction mixture was evaporated in vacuo to a small volume (~3 mL) and DMF (6 ml) was added. The solution was transferred to the above solid which had been dissolved prior to this transfer in DMF (5 mL) and triethylamine (3 mmol). The reaction mixture was stirred at room temperature for 3 hours and to it was then added water:methanol (1:2 v/v, 20 mL) and the mixture was evaporated in vacuo. Methanol (3 mL) was added and the mixture was filtered and the filtrate was collected. The filtrate was purified on preparative silica plates (1 mm thick) using methanol:methylene chloride (20:80) which gave Compound 4 (0.083 g).

A mixture of 10% Pd-C (10% by weight, 100 mg) and Compound 22 (0.683 mmol) resolved by using (−)(S)-α-methylbenzylamine) in methanol (10 mL) was stirred at room temperature under an atmosphere of hydrogen for 3 hours. The catalyst was filtered out through a pad of celite, washed with methanol (10 mL) and water:methanol (1:9, 5 mL). All solvents were combined and evaporated in vacuo to a solid.

In a separate flask, 6-N-Acetyl n caproic acid (4.05 mmol) was dissolved in a mixture of methylenechloride (25 mL) and DMF (3 mL). To this solution was added DCCl (2 mmol) in methylenechloride (10 mL). After one hour stirring at room temperature, the reaction mixture was evaporated in vacuo to a small volume (~3 mL) and DMF (6 ml) was added. The solution was transferred to the above solid which had been dissolved prior to this transfer in DMF (5 mL) and triethylamine (3 mmol). The reaction mixture was stirred at room temperature for 3 hours and to it was then added water:methanol (1:2 v/v, 20 mL) and the mixture was then evaporated in vacuo. Methanol (3 mL) was added and the mixture was filtered and the filtrate was collected. The filtrate was purified on preparative silica plates (1 mm thick) using methanol:methylene chloride (20:80) which gave Compound 5 (0.083 g).

The synthesis of Compounds 4 and 5 was confirmed by spectroscopy—$^1$H NMR ($CD_3OD$) δ 1.20 (d, 3H), 1.35 (m, 2H), 1.50 (m, 2H), 1.60 (m, 2H), 1.90 (s, 3H), 2.30 (t, 2H), 2.65 (m, 1H), 3.15 (m, 1H), 3.90 (m, 1H), 6.70 (bd, 1H), 7.20 (m, 5H),

EXAMPLE 6

Synthesis and Preparation of Inhibitor Compound 6

The synthesis of inhibitor compound 6 followed the same chemical reaction sequence as the synthesis of hapten compound 3, RT-2, except that acetic anhydride was substituted for the symmetrical anhydride of 6-maleimidocaproic acid (24). The correct synthesis of 6 as its triethylammonium salt was confirmed by spectroscopy—$^1$H NMR ($D_2O$) δ 1.25 (t, 9H), 1.75 (s, 3H), 2.75 (m, 1H), 3.20 (m, 7H), 3.55 (d, 3H), 4.25 (m, 1H), 7.25 (m, 5H).

EXAMPLE 7

Synthesis and Preparation of Inhibitor Compound 7

The synthesis of inhibitor compound 7 followed the same chemical reaction sequence as the synthesis of hapten compound 8, WH-2, except that acetic anhydride was substituted for the symmetrical anhydride of 6-maleimidocaproic acid (24). The correct synthesis of 7 as its triethylammonium salt was confirmed by $^1$H NMR spectroscopy.

EXAMPLE 8

Synthesis and Preparation of Substrate Compounds 11 Through 16

Preparation of compounds 11 and 12 followed the synthetic procedure described for compound 9 (FIG. 8) except

17 that N-t-BOC-L-phenylalanine methyl ester and N-t-BOC-D-phenylalanine methyl ester were used, respectively, rather than N-t-BOC-L-Phenylalanine amide 32.

Preparation of compound 13 followed the same synthetic procedure as for compound 9 except that acetic anhydride was used rather than compound 31.

Preparation of compound 14 followed the same synthetic procedure as for compound 9 except that N-t-BOC-D-phenylalanine amide was used instead of N-t-BOC-L-phenylalanine amide 32 and that acetic anhydride was used rather than compound 31.

Preparation of compound 15 followed the same synthetic procedure as for compound 9 except that N-t-BOC-L-phenylalanine methyl ester was used in place of compound 32 and acetic anhydride was used in place of compound 31.

Preparation of compound 16 followed the same synthetic procedure as for compound 9 except that N-t-BOC-D-phenylalanine methyl ester was used in place of compound 32 and acetic anhydride was used in place of compound 31.

EXAMPLE 9

Synthesis and Preparation of Haptens Corresponding to Other Amino Acids

Figure 6:
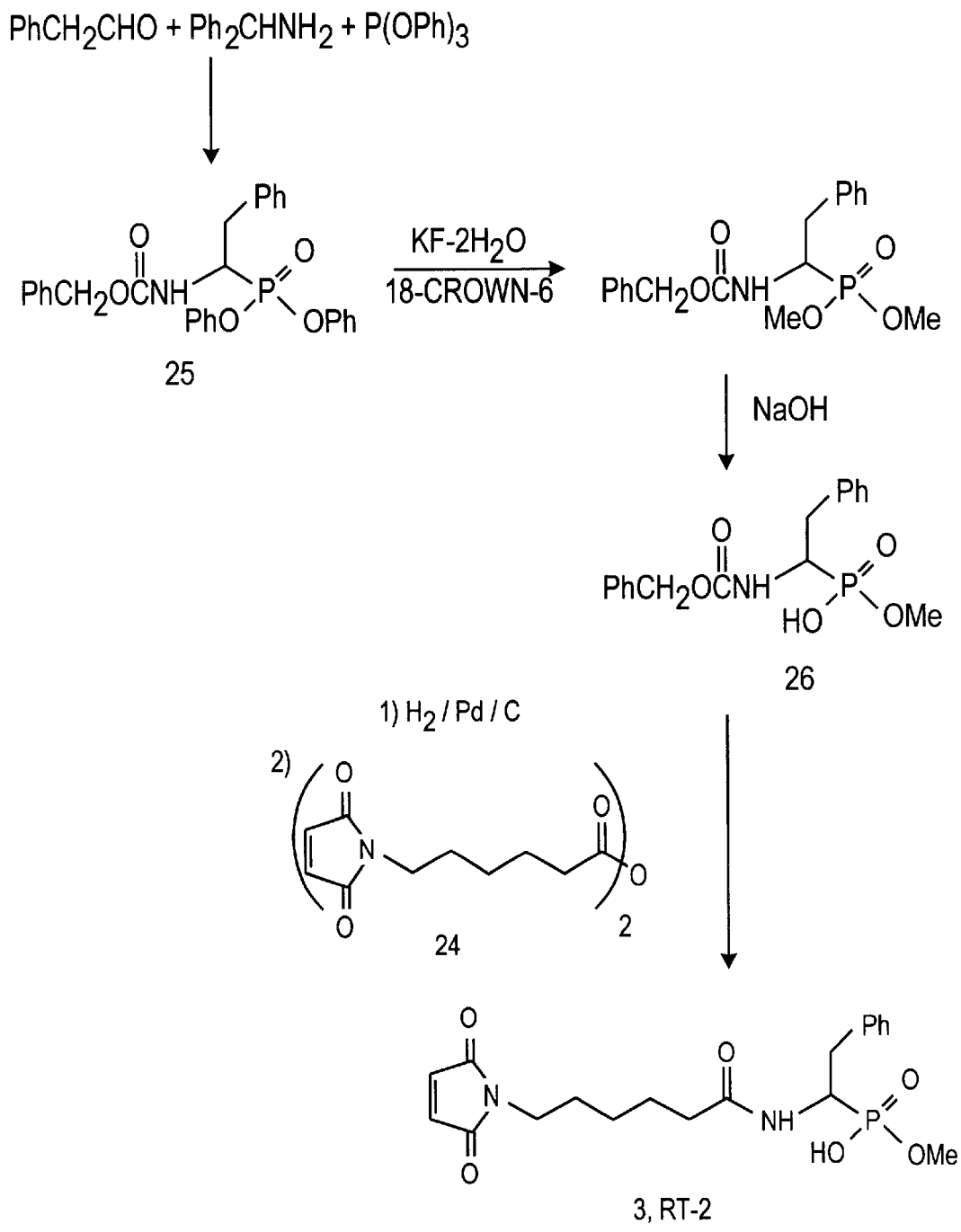

A wide range of different 1-aminoalkylphosphonous acids (e.g., compound 19, FIG. 3) useful in the synthesis of transition-state analog haptens for the elicitation of catalytic antibodies specific for the deamidation of many different amino acids have been described in the scientific literature (e.g., E. Baylis et al., *J. Chem. Soc. Perkin Trans* 1, 12, (1984):2845–2853). Such 1-aminoalkylphosphonous acids can be used as intermediates in the synthesis of haptens corresponding to each of the naturally occurring amino acids. Subsequent chemical reactions in the synthesis of such haptens using these compounds rather than 19 as depicted in FIG. 4 yield NA-1 versions of other amino acids. Alternatively, as revealed by E. Baylis et al., oxidation of the 1-aminoalkylphosphonous acids with either mercuric chloride of bromine water produces the corresponding 1-aminoalkylphosphonic acids. Conversion of the latter to RT-2 versions of other amino acids follows the sequence of 1) amino protection using benzyl chloroformate, 2) O-methylation using trimethylsilyidiazomethane in methanol and 3) hydrolysis with. NaOH to give methylphosphonate versions of other amino acids (analogs of compound 26, FIG. 6). Continuation of the reaction scheme as depicted in FIG. 6 yields the RT-2 hapten version of the desired amino acid.

Figure 7:
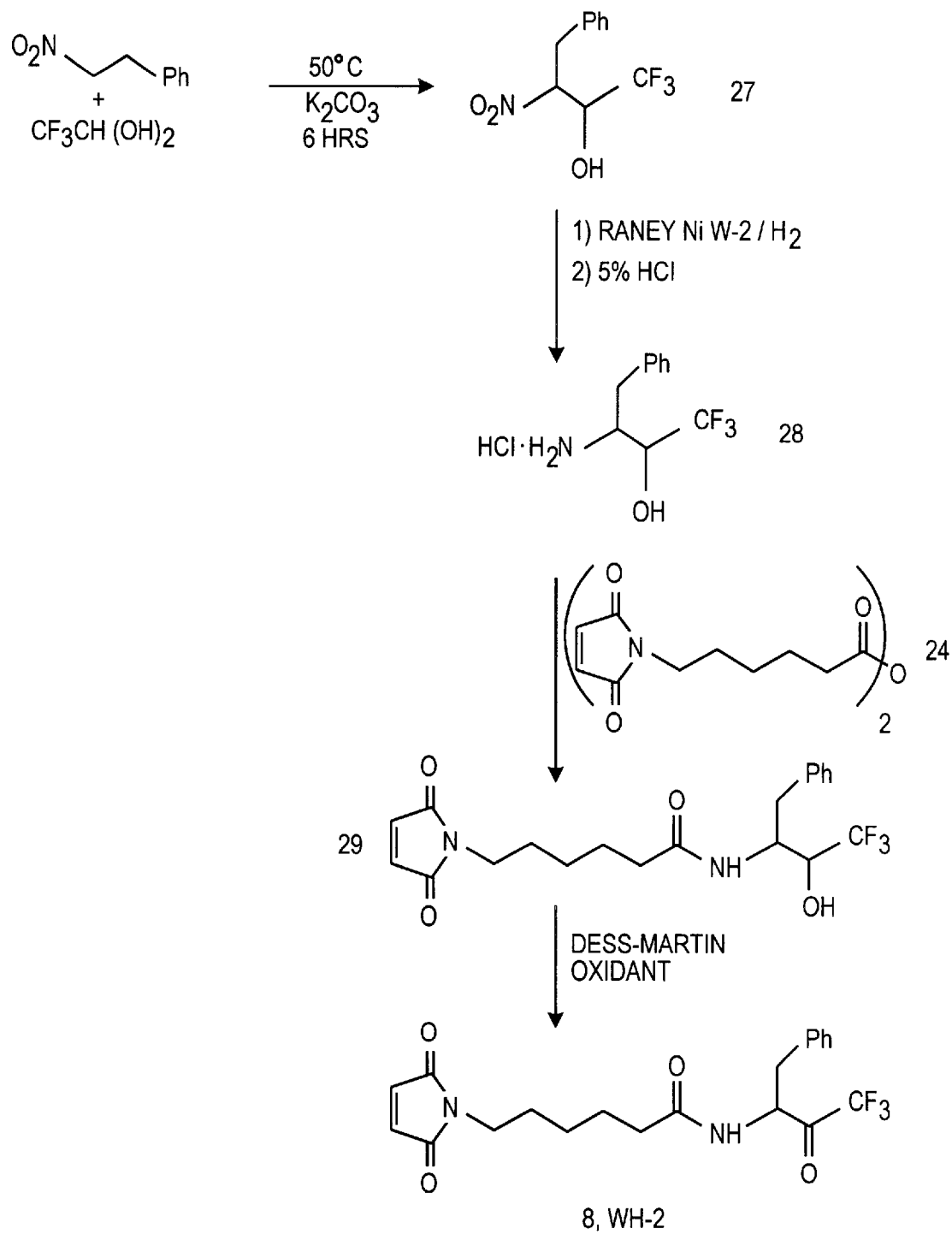

WH-2 versions of haptens corresponding to other amino acids are synthesized by the method depicted in FIG. 7 by substituting the proper nitro compound (corresponding to the side chain of the desired amino acid) in the first step of the synthesis. One of ordinary skill in the art of organic synthesis can readily prepare appropriate nitro compounds to generate the desired amino acid analogs.

EXAMPLE 10

Incorporation of Haptens into Peptides

Incorporation of all transition-state analogs described herein, i.e., compounds of formula (I), (II), and (III), is readily accomplished by those of ordinary skill in the art without undue experimentation. Standard techniques are commonly described in the scientific literature; by way of example, the inventors refer to J. Jones, The Chemical Synthesis of Peptides, Clarendon Press:Oxford, 1991.

EXAMPLE 11

Synthesis and Preparation of Peptides Containing Transition-State Analogs in Amino Acid Side Chains Asparagine Side Chain Analogs Synthesis of a protected dimethylphosphonate asparagine compound, namely (S)-3-(dimethylphosphono)-2-((9-fluoroenyl)methoxycarbamoyl) propionic acid, has been described by J. Hutchinson, et al. (Tet. Lett., 1992, 33, 7065–7066), hereby incorporated herein by reference. This asparagine analog is incorporated in peptides or protein by standard peptide synthesis techniques well known to those of ordinary skill in the art (see, for example, J. Jones, *The Chemical Synthesis of Peptides*, Clarendon Press:Oxford, 1991). Treatment of the peptide with lithium hydroxide hydrolyzes one of the —OMe groups from the phosphonate to yield the RT-2 type hapten in the side chain of asparagine in the peptides.

Synthesis of the analogous NA-1 hapten version is achieved according to the procedure described by J. Hutchinson, et al. (Tet. Lett., 1992, 33, 7065–7066) except that $CH_3(Me_3SiO)P(OMe)$ is substituted for $(ME_3SiO)P(OMe)_2$ in the synthetic procedure. Incorporation in a peptide by standard techniques and subsequent hydrolysis with lithium hydroxide yields the peptide with the NA-1 hapten in the side chain of asparagine.

Figure 11:
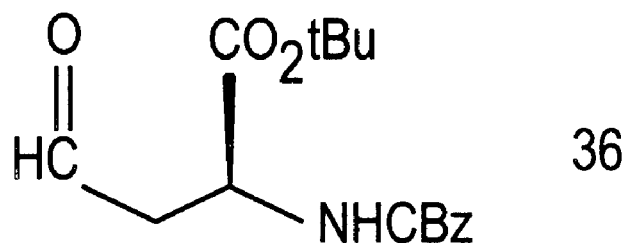
FIG. 11 depicts the synthesis of the trifluoroketone analog in the side chain of asparagine.
Figure 11:
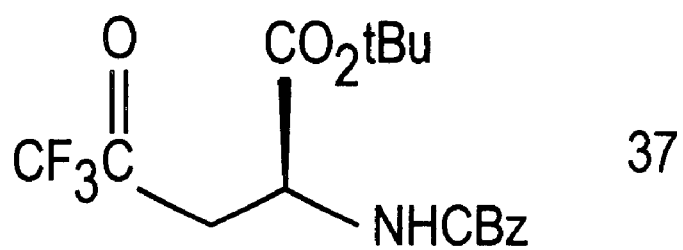

Synthesis of the trifluoro ketone analog in the side chain of asparagine is shown in FIG. 11. The synthesis of 36 is according to the procedure of G. Coppola et al. (*Asymetric Synthesis*, p. 209, John Wiley:New York, 1987), hereby incorporated herein by reference. Conversion of 36 to the desired trifluoro ketone compound is according to the procedure of P. Edwards (Tet. Lett., 1992, 33, 4279–4282), hereby incorporated herein by reference. Accordingly, 36 is first treated with $CF_3ZnI$ and oxidized with Dess Martin Periodinane, yielding the trifluoroketone derivative 37. Compound 37 can be readily incorporated into peptides using standard procedures by deprotection and standard peptide synthetic techniques (see, for example, J. Jones, *The Chemical Synthesis of Peptides*, Clarendon Press:Oxford, 1991).

Glutamine Side Chain Analogs

Figure 12:
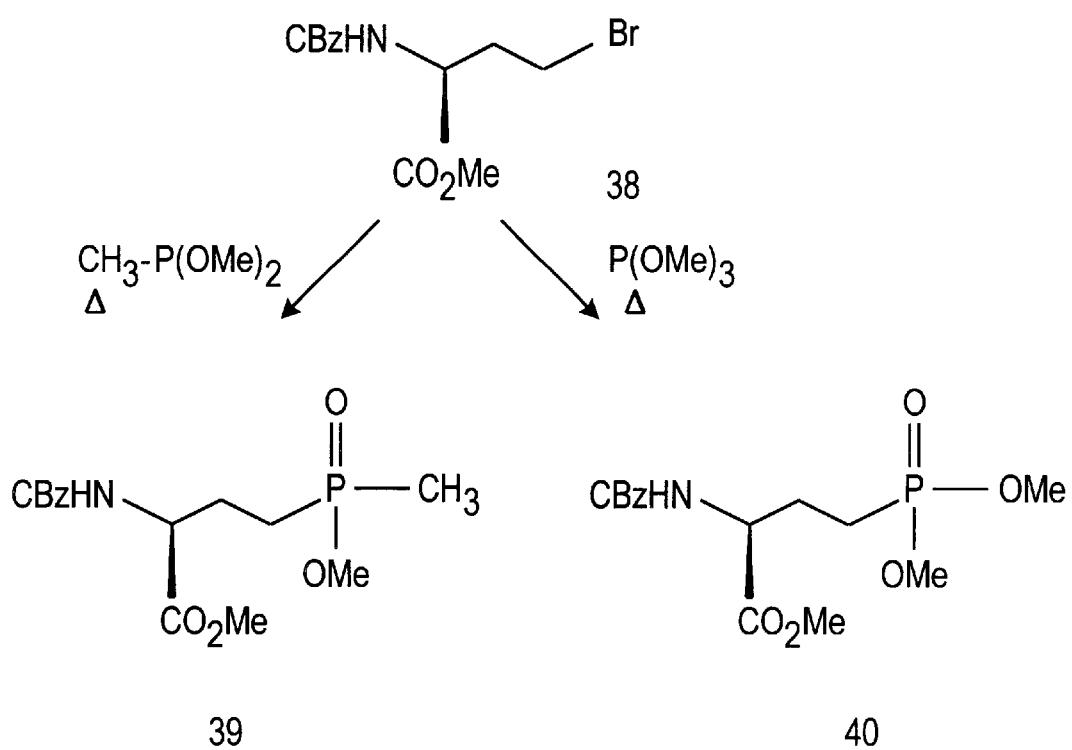

The synthesis of the phosphorous analog in the side chain of glutamine is depicted in FIG. 12. Synthesis of the bromo derivative 38 has been reported by G. Coppola et al. (*Asymetric Synthesis*, p. 222, John Wiley:New York, 1987). Synthesis of the NA-1 hapten version in the side chain of glutamine is achieved by the Arbusor reaction of 38 with dimethylmethylphosphite to yield 39, while the RT-2 version is synthesized using trimethyl phosphite to yield 40. Both phosphorous derivatives are extended into peptides and proteins using standard techniques after deprotection with catalytic hydrogenation using Pd-C to remove the CBz group and NaOH to remove the methyl ester group. Final deprotection of the phosphorous methoxy group(s) is achieved with trimethylsilylbromide yielding the desired haptens in the side chain of glutamine.

Figure 13:
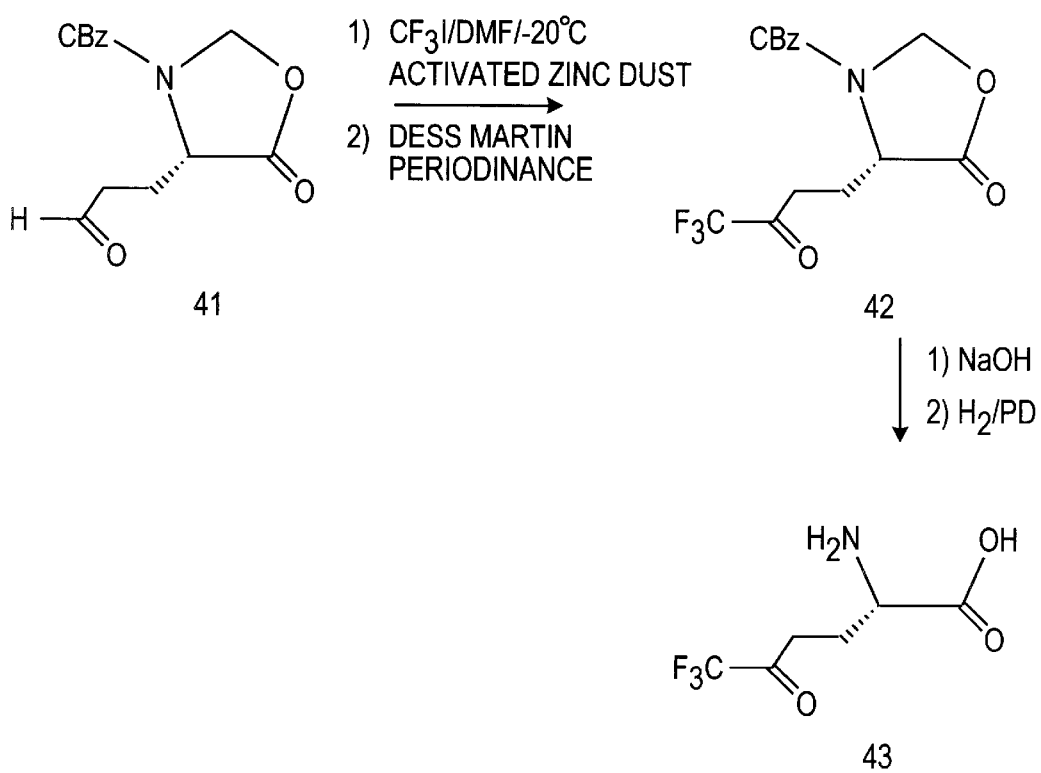
FIG. 13 depicts the synthesis of the trifluoroketone analog in the side chain of glutamine.
Figure 14:
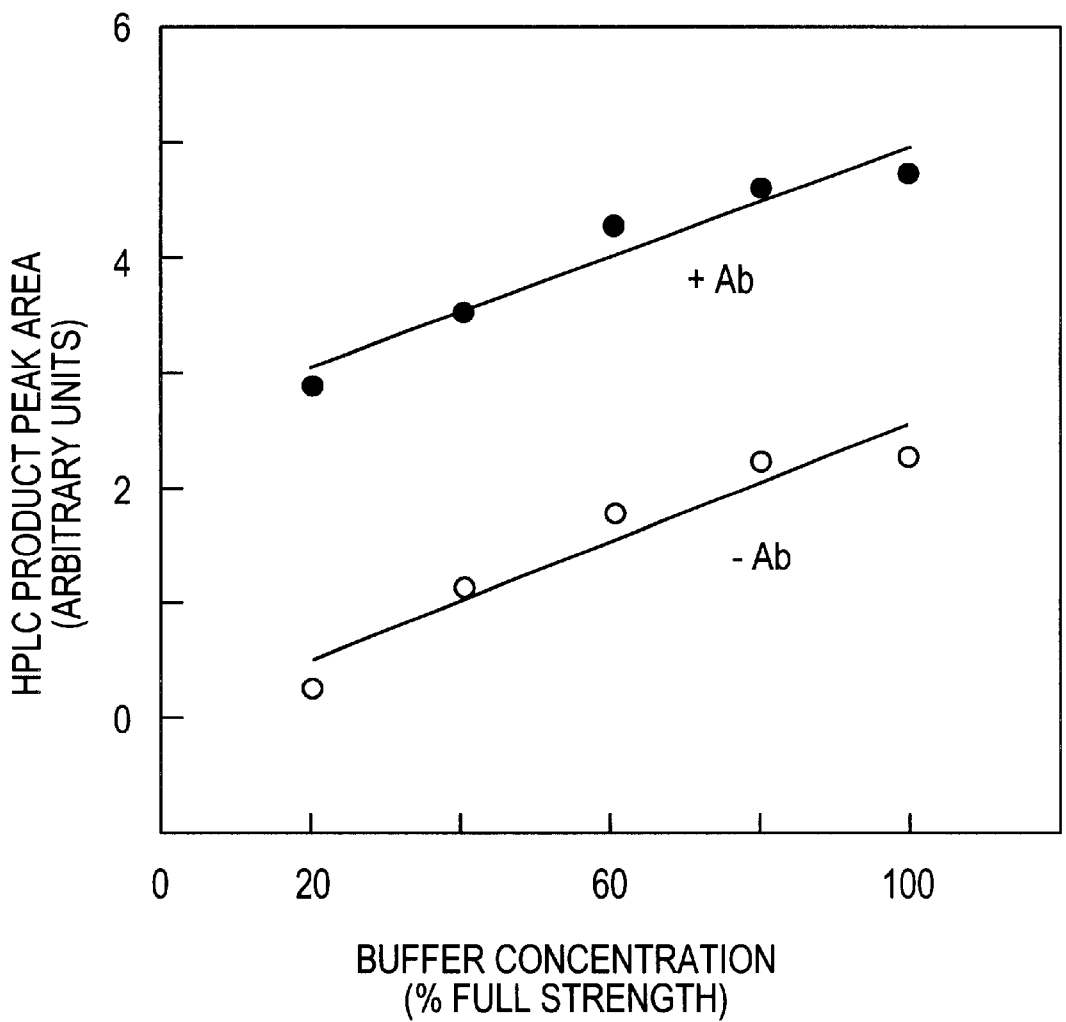
FIG. 14 shows defeat of buffer concentration of catalyzed and uncatalyzed amide hydrolysis.

The synthesis of the trifluoroketone analog in the side chain of glutamine is depicted in FIG. 13. Synthesis of the aldehyde 41 has been reported by G. Coppola et al. (*Asymetric Synthesis*, p. 220, John Wiley:New York, 1987). Reaction of 41 with $CF_3ZnI$ reagent as reported by P. Edwards (Tet. Lett., 1992, 33, 4279–4282) followed by oxidation with Dess Martin periodinane yields the trifluoroketone derivative 42. Ring opening is achieved using NaOH and the fully deprotected trifluoroketone amino acid is obtained after catalytic hydrogenation with 10% Pd-C to yield the trifluoroketone analog of glutamine, compound 43.

Incorporation of each of these side chain analogs into peptides is readily accomplished by those of ordinary skill in the art (see, for example, J. Jones, *The Chemical Synthesis of Peptides*, Clarendon Press:Oxford, 1991).

PRODUCTION OF CATALYTIC ANTIBODIES

Following synthesis of the hapten compounds, conjugates with suitable carrier proteins were prepared and immunization of mice was performed. Hybridomas were prepared from spleen cells of the immunized mice and screened for binding to hapten. Those clones which demonstrated binding affinity for the haptens were subjected to an early screening for catalysis as well as a secondary screening. Fab' fragments were prepared from one antibody which catalyzed the hydrolysis of the primary amide bond in the substrate of FIG. 2.

EXAMPLE 12

Preparation of Transition State Analog Hapten Conjugations

The NA-1 hapten was conjugated to bovine serum albumin (BSA) and keyhole limpet hemocyanin (KLH), via the maleimide-group attached to the linker of the hapten. This was accomplished by modifying the BSA and KLH carrier proteins with Traut's reagent (2-iminothiolane HCl), which replaced the N-terminal amine of groups such as lysine with amidine-linked sulfhydryl groups, and then the modified proteins were mixed with the maleimide-hapten.

More specifically, approximately 5 mg of each protein was dissolved in 1 ml of 50 mM sodium phosphate, pH 8.4. The BSA was combined with 0.25 ml of an 8 mg/ml solution of Traut's reagent in 1M triethanolamine, pH 8.1. The KLH was mixed with 0.5 ml of the Traut's reagent. BSA was incubated for 90 min at room temperature and the KLH for 120 min at room temperature. The reaction was stopped and the modified protein recovered by desalting on a PD-10 column (Pharmacia) equilibrated with 0.1 M sodium phosphate buffer, pH 6.5. A small sample of each of the modified proteins was saved for a free thiol assay. The hapten (5 mg) was dissolved in 0.1 M sodium phosphate buffer, pH 6.5, and then divided between the two proteins. The mixture was stirred at room temperature for 2 hours and then dialyzed against phosphate buffered saline (PBS) at 4° C. with two exchanges of the dialysate.

After the dialysis, the protein concentrations of the modified proteins and the hapten-protein conjugates were determined by the micro-bicinchonic acid assay using BSA as the protein standard. The concentration of free thiols for all four modified proteins was determined with Ellman's reagent using cysteine as the standard. Before hapten conjugation, each mole of the modified BSA contained 33 moles of free thiol and after conjugation to the hapten 10 moles remained. Before conjugation, each mole of modified KLH contained 20 moles of free thiol and after conjugation 5 moles remained. Therefore, the hapten to protein ratio was calculated to be 23:1 for the NA-1-BSA conjugate and 15:1 for the NA-1-KLH conjugate, using a molecular weight of 64,000 for both proteins.

EXAMPLE 13

Immunizations

BALB/cAnN female mice, 11-weeks-old, were injected intraperitoneally with 20 µg of NA-1-KLH emulsified in complete Freund's adjuvant. The mice were boosted with 20 µg of NA-1-KLH emulsified in incomplete Freund's adjuvant after four weeks. The immune response after the second injection was determined by ELISA. The inverse IgG titer of the antiserum against NA-1-BSA was 51,200 (dilution which gives 50% maximum optical density). The mice were boosted 7 months later with 10 µg of antigen in PBS intrasplenically.

EXAMPLE 14

Hybridoma Production and Screening

One mouse was sacrificed three days after the last injection and the spleen used as a source of splenocytes for production of hybridomas. SP2/0 cells were used as the fusion partner. After 11 days of growth, the hybridoma supernatant fluids were assayed for specific antibodies against NA-1-BSA by ELISA. Of the 4149 colonies obtained, 384 hybridomas produced IgG antibodies which reacted with the conjugate. These cells were expanded and re-assayed 7 days later for binding to NA-1-BSA, BSA and KLH. Seventy-one hybridomas produced antibodies which could bind to NA-1-BSA but did not react with BSA or KLH. These hybridomas were expanded further for freezing. The supernatant fluids from these hybridomas were collected from the cells for catalytic activity assays.

The hybridomas which appeared to be producing antibodies with catalytic activity were cloned by limiting dilution. Clones were expanded for ascites fluids production in BALB/cAnN mice previously primed with 0.5 ml of pristane (2,6,10,14-tetramethylpentadecane). Each mouse was injected with $5 \times 10^5$ hybridomas and the ascites fluids collected and pooled.

EXAMPLE 15

Preparation of 13D11 Fab' Fragment

One ml of 13D11, a catalytic antibody which was shown to catalyze the hydrolysis of primary amides, at 5.8 mg/ml was combined with 0.11 ml of 1M citrate buffer, 1.5 M NaCl, pH 3.6. Insoluble pepsin-agarose (15 mg; 21 units/ml solid) was resuspended and washed with 0.1 M citrate buffer, 0.15 M NaCl pH 4.2. The antibody and pepsin-agarose were combined at 37° C. for 15 hours. The reaction was stopped by adjusting the pH to 7.5 with 3 M Tris-HCl buffer, 0.15 M NaCl, pH 8.5. The extent of the digestion was checked by FPLC gel filtration chromatography on a Superose 12 prepacked HR10/30 column. All of the antibody was digested to Fab'$_2$ after the overnight incubation. The Fab'$_2$ was converted to Fab' by stepwise reduction with 10 mM cysteine for 1 hour at room temperature and alkylation with 30 mM iodoacetamide for 2 hours at room temperature. The Fab' fragments were purified by gel filtration on the Superose 12 column equilibrated with 0.1 M Na phosphate, buffer 0.14 M NaCl, pH 7.0. All the column fractions were assayed for antibody binding to NA-1-BSA by ELISA using a Fab' specific secondary antibody (goat anti-mouse Fab') labeled with peroxidase. The peak Fab' fractions were pooled and concentrated with a Centriprep-10 concentrator.

EXAMPLE 16

WH-2 and RT-2 Conjugation and Antibody Generation

The WH-2 and RT-2 haptens were conjugated to BSA and KLH in a manner similar to NA-1. The conjugation ratio for WH-2 was 38:1 for WH-2;BSA and 11.5:1 for WH-2;KLH. The ratio for RT-2 was 22:1 for RT-2;BSA and 8:1 for RT-2;KLH. BALB/c mice were immunized in a similar manner to NA-1-KLH, and an immune response generated. Hybridomas were produced and selected as described above for NA-1.

EXAMPLE 17

Initial NA-1 Antibody Catalytic Selection

An early screen protocol was used to select a subset of potentially catalytic antibodies from the large number of antibodies that had been selected on the basis of hapten affinity. The procedure entailed screening antibodies present in hybridoma supernatants for catalytic activity. Because antibody in culture supernatants is very dilute (typically 1–10 μg antibody per mL) and impure (potentially containing adventitious enzymes that may catalyze the reactions), the results of the procedure are usually improved if the antibodies are concentrated and purified before they are assayed. Both concentration and purification were carried out quickly and conveniently by immobilizing and washing the antibodies on anti-mouse IgG affinity gel.

a) Preparation of the Supernatants for Immobilization: A total of 68 hybridoma supernatants were extracted from exhausted cultures and the pH of each was adjusted to 7.0–7.5 with 2N NaOH. Cell debris was removed by centrifugation for 30 min. at 2700 rpm and supernatants were decanted into polypropylene tubes. Total volumes of the supernatants varied between 4.0 and 13.2 mL (mean=10.8 mL). Each supernatant was then divided into four equal aliquots in individual 15-mL polypropylene tubes (4×68= 272 tubes). The 4 sets of 68 supernatants were frozen at −700° C. until immobilized on affinity gel.

b) Antibody Immobilization: The following immobilization procedure was done four times, each time using one of the four sets of 68 aliquoted supernatants described above. Anti-mouse immunoglobulin affinity gel (Calbiochem, binding capacity 0.5–2.0 mg of immunoglobulin per mL of gel) was added to each tube as a 50% slurry in PBS (140 μL containing 70 μL gel) and the resulting suspensions were mixed gently for 16 hours at room temperature. After 16 hours, a 96-well Millititer GV filtration plate (Millipore) was pre-wetted and washed in PBS containing 0.05% Tween-20. The affinity gel suspensions were spun in a centrifuge at 2500 rpm for 15 min., the bulk of the supernatant was removed by aspiration, and the residual slurries (250 μL) from each polypropylene tube were each transferred to separate wells in the filtration plate. Residual supernatant was removed by aspiration through the plate and the immobilized antibody was washed at 4° C. with PBS/Tween (5×200 μL), PBS (3×200 μL), and 25 mM HEPES, pH 7.2 (3×200 μL).

c) Incubation of Immobilized Antibodies and Substrate: Because of the large number of desired assays (68 antibodies×8 substrates×3 pH values=1632 assays) the following strategy was adopted to accelerate the screening process and economize on immobilized antibody. As described above, four filter plates were prepared, each containing the 68 immobilized antibodies. To reduce the required number of assays in half, the D and L isomers of each of the four types of substrates were mixed and the D/L mixtures of each substrate were assayed together (8 individual substrates were thus reduced to 4 mixtures). Each plate was dedicated to a D/L mixture of a single type of substrate but used three times at three different pH values; pH 7.0, 5.0, and 9.0. To immobilized washed antibody in the filtration plate was added 100 μL of D and 100 μL of L substrate, both in 200 μM stock solutions in 25 mM Hepes, pH 7.0, 140 mM NaCl, 0.01% NaN$_3$. The plates were incubated at room temperature (approximately 220° C.) for approximately 24 hours (for both amides and esters). Following the incubation, the substrate solution (but not beads) was withdrawn and frozen (−20° C.) until later analyzed by either TLC or HPLC as described below. The same 96 well plate, still containing immobilized antibody, was washed with 4×200 μL/well with 25 mM MES, pH 5.0, 140 mM NaCl. Again, 100 μL of 200 μM of both D and L substrate was added (200 μL total volume), this time in the pH 5.0 buffer. Incubation at room temperature was carried out for approximately 24 hours (amide substrates) or 14 hours (ester substrates). Substrate solution was withdrawn and frozen at pH 7.0 until analysis for product formation. Finally, using the same immobilized antibody, the procedure was repeated at pH 9.0 in 25 mM Tris, 140 mM NaCl. The substrate mixture was incubated with immobilized antibody for 24 hours (amides) or for 3 hours (esters), after which time the substrate solutions were withdrawn and frozen until analyzed.

d) Analysis of Reaction Mixtures for Product Formation: Reaction mixtures were analyzed for product formation either by TLC (dansylated substrates) or HPLC (acetylated substrates).

i) TLC Substrate mixtures were centrifuged briefly in an Eppendorf centrifuge to prevent any carry-over of the affinity beads. Samples were spotted onto a TLC plate (HPTLC Silica Gel 60 pre-coated plates (E. Merck, Darmstadt), with concentrating zone) and developed in a solvent system of (by volume) 90% acetone, 8% methanol, and 2% triethylamine. After air drying, the plates were dipped in 20% triethanolamine in isopropanol and again air dried. Fluorescent spots were visualized under UV irradiation in a darkroom. Because substantial uncatalyzed formation of product was sometimes seen, especially with ester substrates at pH 9.0, identification of positives was judged subjectively. A positive result was one in which the intensity of the TLC product spot was judged to be substantially brighter than the product spot in the lane representing a reaction mixture that contained substrate but no antibody.

ii) HPLC Substrate mixtures were centrifuged briefly in an Eppendorf centrifuge to prevent any carry-over of the affinity beads onto the HPLC system. An analytical reverse phase column (Vydac 218TP54 C18) was used to separate substrate and product on a Waters HPLC system. Analytes were separated using a linear gradient over 20 minutes from 85% water/15% acetonitrile to 28% water/72% acetonitrile. All HPLC solvents contained 0.1% TFA. Product was detected and quantitated spectrophotometrically using a Waters 490 Multiwavelength Detector, typically set at 215 and/or 260 nm. Product peak areas were quantitated and varied substantially.

d) Choice of Antibodies to Screen Further Many of the antibodies showed potential activity toward at least one substrate. It was decided to pursue further those antibodies which showed activity in the greatest number of experiments. To facilitate this decision, Table III was prepared. Antibodies were chosen both on the basis of total number of positives (shown in Table), for consistent positive results for a given type of reaction (e.g., esterolysis), or consistency for a given pH. The 8 antibodies chosen for continued study are denoted by asterisks;

TABLE III

Positive Assays in Screening of NA-1 Antibodies.
Antibodies were generally screened 12 times (3 pH values × 4 substrate mixtures).

| Antibody | # Positives | Antibody | # Positives | Antibody | # Positives |
|---|---|---|---|---|---|
| 28E8 | 1 | 9H12 | 3 | 29B11 | 3 |
| 5B11 | 1 | 19D7 | 1 | 30G7 | 3 |
| 24F2 | 2 | 8C2 | 2 | 16D6 | 3 |
| 15F7 | 1 | 9H11 | 1 | 30D6 | 4 |
| 16E9* | 6 | 21F6 | 2 | 29G6 | 2 |
| 11C1 | 1 | 2E1* | 5 | 14E10 | 1 |
| 16D7 | 1 | 19H5 | 1 | 13F12* | 3 |
| 8B8 | 0 | 16H12 | 1 | 14B3 | 2 |
| 11D10* | 6 | 18C7 | 1 | 27B9 | 1 |
| 1G10 | 4 | 11F3* | 4 | 9C12 | 3 |
| 14D12 | 0 | 6F12 | 0 | 26D3 | 3 |
| 11B6 | 0 | 13E4 | 2 | 27F4 | 1 |
| 3B4 | 4 | 18E1 | 0 | 12D2 | 0 |
| 6G8 | 2 | 24B2 | 3 | 28C9 | 4 |
| 10A10 | 2 | 6F8 | 1 | 23H5* | 5 |
| 14A8* | 6 | 2B3 | 4 | 20C12 | 1 |
| 2F4 | 2 | 26B10 | 3 | 7E5 | 0 |
| 13D11* | 4 | 3C4 | 3 | 6D1 | 1 |
| 1F4 | 1 | 27B1 | 1 | 5H9 | 2 |
| 20C11 | 3 | 24G8 | 1 | 20F12 | 2 |
| 19E10 | 2 | 9A12 | 3 | 12E3 | 3 |
| 2F4 | 1 | 20A1 | 2 | 213C8 | 2 |
| 12C8 | 4 | 8C3 | 4 | | |

*Selected for further screening.

EXAMPLE 18

Secondary Screening of NA-1 Antibodies for Catalytic Activity

To further examine the antibodies selected from the early screen for catalytic activity, the proteins identified in the early screen were individually grown in ascites and purified. Unfortunately, 2 of the 8 chosen cell lines were unable to produce antibody for further testing (16E9 and 2E1). Initially, the following four antibodies were prepared and screened; 125NA-1K-13D11-2F9 ("13D11"), 125NA-1K-14A8-1A2 ("14A8"), 125NA-1K-23H5-2C7 ("23H5"), and 125NA-1K-11D10-4F6 ("11D10"). Assays were performed in the same buffer systems and pH values as in the early screen but the antibodies were tested individually and they were not immobilized but free in solution.

Monoclonal antibodies (13.5–15.0 $\mu$M in the reactions) were first individually assayed at 37° C. and pH 7.0 (25 mM HEPES, 140 mM NaCl, 0.01% NaN$_3$) with 9 (500 $\mu$M), 10 (500 $\mu$M), 13 (1.0 mM), 14 (1.0 mM), 15 (1.0 mM), and 16 (1.0 mM). Dansyl substrates were screened by TLC and acetyl substrates were screened by HPLC as described above. None of the antibodies showed any hydrolysis above background toward 9 or 10 after 3 days. One antibody, 11D10, showed some activity toward 15 and 16 but this activity was not inhibited with 6 suggesting that the activity was due to a contaminating esterolytic enzyme. Compound 6, which closely resembles the haptens 1was used because hapten-based inhibitors 4 and 5 were not then available. After 4 days, 13D11 alone showed activity toward 10. None of the antibodies showed any activity toward 9.

The four NA-1 antibodies were individually re-screened at pH 5.0, 7.0, and 8.8 toward the four amide substrates 9,10,13, and 14. Antibody combining site concentrations were; 13D11=14.5 $\mu$M, 14A8=14.8 $\mu$M, 23H5 =15.0 $\mu$M, and 11D10=6.8 $\mu$M. The reaction was run at room temperature and product formation was measured at 13 or 16 days. After 16 days, no activity was seen toward 13 or 14 at any pH with any antibody. Only 13D11 showed activity toward 10 and only at pH 8.8 (13 days). No antibody showed activity toward 9 at any pH (13 days).

Antibody 13D11 (14.5 $\mu$M) was re-screened for activity toward 10 (nominally 500 $\mu$M) in the absence and presence of 63 $\mu$M (RT-2 hapten)(D/L mixture). The activity was estimated to be inhibited approximately 50% by 3, RT-2 CHES buffer was tried as an alternative to Tris but was found to inhibit the hydrolysis of 10 by 13D11. Antibody 23H5 re-screened together with 13D11 showed no activity toward 10.

Until this point, 13D11 antibody had been purified by Protein A and DEAE chromatography. To determine whether the activity toward 10 was due to a contaminating enzyme, 13D11 was further purified on a Mono Q column (Pharmacia) by FPLC. The antibody retained activity toward 10 which was inhibitable by 6, although some hydrolysis was seen in controls. Later experiments showed no hydrolysis in controls indicating that this was probably due to laboratory contamination of the controls.

Attempts to quantitate the rate of 10 hydrolysis by 13D11 using the Waters HPLC system failed. Instead of a single product peak, multiple small peaks were detected. The substrate 10 was designed for early detection based on its potent fluorescence rather than its meager molar extinction coefficient ($\epsilon_{328}$=2100 M$^{-1}$cm$^{-1}$) which was measured with the HPLC. The occurrence of multiple peaks is believed to result from anomalous behavior of the nonpolar dansyl group under HPLC conditions.

The final two untested antibodies chosen from the early screen were grown in ascites, purified, and assayed individually. The antibodies, designated 125NA-1K-11F3-1A8 ("11F3") and 125NA-1K-13F12-2F3 ("13F12"), were assayed at pH 5.0 (100 mM sodium acetate, 140 mM NaCl, 0.01% NaN$_3$), pH 7.0 (100 mM HEPES, 140 mM NaCl, 0.01% NaN$_3$), and pH 9.0 (100 mM Tris, 140 mM NaCl, 0.01% NaN$_3$). Each antibody was assayed with the dansylated substrates 9, 10, 11, and 12 (×3 pH values=12 assays). Initial substrate concentrations were 200 $\mu$M and antibody concentrations were 18.4 $\mu$M (11F3) and 3.4 $\mu$M (13F12). The results of the ester hydrolysis assays showed no activity above background for either antibody after 3 hours at pH 9.0 or after 24 hours and 5 days, both at pH 7.0. There was no apparent activity at pH 5.0 after 24 hours but after 5 days at pH 5.0 there appeared to be some hydrolysis of 12 by 11F3. Neither antibody showed activity toward the amide 10 after 6 days at pH 5.0, 7.0, or 9.0, but 11F3 showed activity toward 9 after 6 days at pH 5.0, 9.0, and possibly 7.0.

A second ascites preparation of 13D11 was purified and assayed for activity toward 10. Initially, no hydrolysis of 10 was seen at pH 9.0 using this new antibody preparation. It was determined that the antibody had been dialyzed by mistake into PBS (10.0 mM phosphate). As a precaution against potential inhibition by phosphate, PBS is routinely avoided in catalytic assays of antibodies raised against tetrahedral phosphorous haptenic groups. Following dialysis into 10 mM HEPES, pH 7.5, 140 mM NaCl, 0.01% NaN$_3$ to remove all phosphate, 13D11 was re-assayed (at pH 9.0 in Tris assay buffer). Hydrolytic activity was now seen when 13D11 was incubated for 7 days with 10. The antibody was also re-assayed with the D- ester, 12. No activity was seen above (relatively rapid) background hydrolysis at pH 9.0.

EXAMPLE 19

Partial Screening of Anti-WH-2 Antibodies for Catalytic Activity

An early screen of antibodies raised against the WH-2 hapten (2) was carried out at a single pH (7.0) with only a subset of the available substrates. The general method of early screening using a 96-well filter plate was as described above. A total of 48 hybridoma supernatants (4 mL each) were shaken overnight at 40° C. with 20 μL of anti-mouse antibody beads (Calbiochem, described above). After washing with buffer, beads were washed with 25 μL of a solution of the dansylated esters 11 and 12 (approx. 100 μM of each in HEPES buffer, pH 7.0). The beads were then incubated with 50 μL of this substrate mixture for 1 hour at 37° C. Reaction mixtures were analyzed on TLC plates as described above and formation of the fluorescent dansylated product was detected by UV illumination. Background product formation was detected in all lanes, but no catalytic activity was apparent. After washing the beads with buffer, a second screen (with the same beads) was carried out with a mixture of the amides 9 (106 μM) and 10 (100 μM)(50 μL total volume at pH 7.0). TLC analysis after 6 hours at 37° C. showed faint background for all lanes, but no catalytic activity for any of the antibodies.

EXAMPLE 20

Partial Screening of Anti-RT-2 Antibodies for Catalytic Activity

An early screen of antibodies raised against the RT-2 hapten (3) was carried out at a single pH (7.0) with only a subset of the available substrates. The general method of early screening using a 96-well filter plate was as described above. A total of 11 hybridoma supernatants (4 mL each) were shaken overnight at 4° C. with 20 μL of anti-mouse antibody beads (Affi-gel beads coated with goat anti-mouse antibody). The mixture was stored at 4° C. for 2 weeks, after which the beads were transferred to 96-well filter plates as described above and washed with phosphate-buffered saline (PBS), PBS containing Tween detergent (3 washes), and MTEN, pH 7.0 (3 washes). MTEN buffer consists of 50 mM MES, 25 mM Tris, 25 mM ethanolamine, 100 mM NaCl.

a) Dansylated D-ester: Beads were washed with 2×50 μM of 18 μM of the dansylated D-ester 12 (MTEN buffer, pH 7.0). Beads (and control wells) were incubated with 50 μL of 18 μM 12 for 12 hour at 25° C. After 5 and 12 hours samples were withdrawn from the wells and screened by TLC for appearance of the carboxylic acid product. After 5 hours no product was seen and after 12 hours product was seen in all lanes, including controls.

b) Dansylated L-ester: After 12 hours incubation with the D-ester, the beads were stored at 4° C. for a further 10 hours, then substrate solution was removed by vacuum filtration, and the beads were washed with 2×50 μL of the dansylated L-ester, 11 (24 μM). Beads and control wells were incubated with 50 μL of 24 μM 11 for 13 hours at 25° C. After 13 hours, product formation was observed by TLC in all reaction mixtures, including controls. No catalysis was apparent.

c) Dansylated D/L-amide: After 13 hours incubation with 11 at 25° C. the beads were filtered dry, washed with MTEN, pH 7.0 (3×200 μL), and prepared for amide hydrolysis screening. A mixture of the D- and L-amides (9 and 10) was prepared in MTEN buffer (pH 7.0). The solution contained 50 μM of each of the two potential substrates. Beads and control well were washed with the 9/10 mixture (2×50 μL) and incubated with 50 μL of the mixture for 15 hours at 25° C. After 15 hours background product was visible by TLC analysis in all lanes, antibody as well as control. None of the antibodies gave rise to product spots that were any brighter than the controls.

None of the RT-2 antibodies showed activity at pH 7.0 with any of the four dansyl substrates, 9–12.

CHARACTERIZATION OF CATALYTIC ANTIBODIES

EXAMPLE 21

Verification and Characterization of 13D11 Catalytic Activity

An attempt was made to determine the kinetic parameters for the hydrolysis of 10 by 13D11. Reaction mixtures containing 25 mM Tris, pH 9.0, 140 mM NaCl, 0.01% $NaN_3$, 6.6 μM 13D11 and various concentrations of 10 (57 μM–514 μM) were incubated at 25° C. for 18 days. The antibody was kept in 10 mM HEPES, pH 7.5, 140 mM NaCl and 0.01% $NaN_3$ prior to addition to the assay mixture. Controls were run parallel to the reaction samples wherein the conditions of the latter were duplicated but the antibody was omitted. Analyses were done by TLC and HPLC as described above. No peak corresponding to product was observed in the HPLC runs of the samples containing the highest concentration of substrate, in which case the samples of much lower concentrations were not subjected to the same analysis. A number of unidentified peaks were observed at 328 nm, possibly due to a peculiarity in the response of the fluorescent reporter group under HPLC conditions, for both the control and reaction samples. The TLC analyses complemented the HPLC results by showing multiple spots in the product region. A later experiment utilizing a higher concentration of antibody (13 μM) gave the same inconclusive results. One factor that may have accounted for the above results was that the experiment was not done at optimum pH. Accordingly, the effect of pH on the hydrolytic activity of 13D11 was investigated and described below:

a) pH Studies: The pH dependence for the hydrolysis of 10 by 13D11 was examined at 25° C. using a constant ionic strength pH 9.0 buffer system containing 100 mM Mes, 50 mM Tris, 50 mM ethanolamine, and 100 mM NaCl (MTEN) to cover the pH range from 6 to 10. EDTA (0.1 mM), PMSF (0.1 mM), and $NaN_3$ (0.01%) were added to ensure a "protease-free" environment. In addition, the incubation mixtures contained 81 μM 10 and 11 μM 13D11. The antibody was dialyzed in a weaker buffer concentration (1 mM HEPES, pH 7.5, 100 mM NaCl, and 0.01% $NaN_3$) and its addition to the reaction mixture did not induce any pH change. Controls were run for each pH unit examined. The TLC analyses showed no hydrolysis of 10 from pH 6 to pH 9.5 when the antibody was omitted from the incubation mixture. However, an uncatalyzed hydrolysis of 10 was noted at pH 10. In the presence of 13D11, hydrolysis of the substrate was observed from pH 8.5–pH 10. The intensities of the fluorescent product were indistinguishable at pH 9 and 9.5 but were stronger than the one at pH 8.5. The hydrolytic activity of 13D11 towards the dansylated substrate 10 was found to be most pronounced at pH 9.

b) Hapten Inhibition: The phosphonate hapten-based inhibitors 4 and 5 were evaluated in terms of their inhibitory effects on the amidase activity of 13D11. The assay mixtures containing MTEN, 0.1 mM EDTA, 0.1 mM PMSF, 0.01% $NaN_3$, 65 μM 10, 10 μM 13D11, and 0–50 μM, Ph 9.0 of either hapten 4 or 5 were incubated for four days at 25° C. and analyzed by TLC. Spotting for TLC was accomplished quantitatively by using the Drummond microcap pipettes (1 μL). Only one of the haptens (assumed to be compound 5 on the basis of the catalytic specificity) completely inhibited the hydrolytic activity of 13D11. The other hapten (assumed to be 4) showed only slight inhibition at the highest concentration used.

c) Substrate Specificity: The substrate specificity of 13D11 was more rigorously determined by monitoring its activity towards the dansylated amides 9 and 10, dansylated esters 11 and 12, acetylated amides 13 and 14, and acetylated esters 15 and 16. The esterolytic activity of 13D11 with the dansylated or acetylated esters (45 $\mu$M-1.0 mM) was examined at 25° C. in an assay mixture containing MTEN, 0.1 mM EDTA, 0.1 mM PMSF, 0.01% $NaN_3$, and 13D11 (7–14 $\mu$M). Aliquots were removed from the incubation mixtures every hour for 4 hours and kept in ice prior to analysis. The dansylated esters were analyzed by TLC while the acetylated esters were subjected to HPLC analysis. The results showed the absence of catalyzed-hydrolysis above background for the esters 12, 15, and 16. Product formation was observed for dansylated ester 11, however, this activity was not inhibited by hapten 5. The observed esterase activity may be due to a trace of a contaminating enzyme in the antibody preparation.

The amidase activity of 13D11 was likewise examined using the same buffer system as the one mentioned above in the presence of 13D11 (17 $\mu$M), and the acetylated amide 13 or 14 (0.5–1.0 mM). The HPLC analyses showed no product formation after 3 days of incubation at 25° C. The ability of 13D11 to discriminate between the dansylated amides 9 and 10 was investigated by determining the formation of the hydrolysis product by TLC. The reaction samples containing 150 $\mu$M of either amide 9 or 10, 30 $\mu$M 13D11, with or without hapten 5 (0.5 mM) in the above buffer system were assayed after 5 days of incubation at 25° C. Analysis showed an intense fluorescent product spot for amide 10 but not for 9. The preference of 13D11 for amide 10 as well as the inhibition of its amidase activity by the phosphonate assumed hapten 5 were confirmed further.

d) Examination of the Activity of 13D11 (Fab'): An important control in the examination of the catalytic activity of 13D11 IgG molecule is the retention of the haptenic and substrate binding abilities by its Fab' fragment. Accordingly, the amidase activities of 13D11 (whole IgG molecule) and the 13D11 Fab' fragment were compared. The reaction mixtures contained MTEN, 1 mM EDTA, 0.1 mM PMSF, 0.01% $NaN_3$, 150 $\mu$M dansylated amide 9 or 10, 30 $\mu$M 13D11 (IgG) or Fab', with or without (assumed) hapten 5 (0.5 mM). TLC analyses done after 3 days (and again after 8 days) showed positive results for both IgG and Fab' with the dansylated amide 10. The amidase activities exhibited by both molecules were inhibited by the phosphonate hapten 5. The esterase activity for the Fab' fragment was also examined in the above buffer system containing 100 $\mu$M of either ester 11 or 12, and 7 $\mu$M 13D11 (Fab'). Aliquots were removed at various time points and analyzed by TLC. No hydrolysis (above background) of the dansylated esters 11 and 12 was observed. The contaminating enzyme in the antibody solution may have been removed during the purification of the Fab' fragment.

THERAPEUTIC USE OF AMIDOLYTIC CATALYTIC ANTIBODIES

EXAMPLE 22

Specific Tissue Targeting of Therapeutic Amidolytic Catalytic Antibodies a) Preparation of bi-specific molecules: Catalytic antibodies capable of hydrolyzing primary amides will sometimes be more therapeutically effective if specifically directed to a tissue target, such as a tumor. Such catalytic antibodies will be capable of hydrolyzing primary amides that are generated and/or consumed by tissues such as tumors and whose destruction results in effective treatment of a disease state. Some therapeutically important amides are described in the background of the invention. Antibodies are conjugated to a molecule that is able to specifically bind to that tissue target, such as a monoclonal antibody which recognizes, as its antigen, a tumor-associated antigen. Conjugation will be by any of a number of well-known chemical crosslinking agents or, if the targeting agent is a protein, by DNA technology. In the latter strategy the catalytic antibody (or fragment thereof) and the targeting agent (e.g., anti-tumor antibody) are expressed as a single fusion protein. Methods of generating chemical crosslinks and fusion proteins are available and can be carried out by one skilled in the art without undue experimentation. In some cases, such as in the use of catalytic antibodies with asparaginase activity used to treat leukemias, it is not necessary to direct the antibody to a particular site for therapeutic effectiveness.

b) Administration of therapeutic bi-specific molecules: The bi-specific molecule consisting of a tissue-targeting molecule such as an anti-tumor antibody and a catalytic antibody capable of hydrolyzing a primary amide bond from a therapeutic target are administered to a patient in such a way as not to destroy the molecule (i.e., intravenous injection is preferred over oral administration). The dosage and frequency of administration will depend on, among other factors, the nature of the disease, the severity of the disease, and the weight, age, and condition of the patient. Dosage and frequency of treatment can be determined without undue experimentation by one skilled in the art.

Having thus described in detail the preferred embodiments of the present invention, it is to be understood that the invention defined by the appended claims is not to be limited by particular details set forth in the above description as many apparent variations thereof are possible without departing from the spirit or scope thereof.

REFERENCES

1. Lerner, R. A. & Benkovic, S. J. (1990) Chemtracts—Org. Chem. 3, 1–36.
2. Scanlon, T. S. & Schultz, P. G. (1991) Phil. Trans. R. Soc. Lond. B 332, 157–164.
3. Schultz, P. G., Lerner, R. A., & Benkovic, S. J. (1990) Chem. Eng. News, May 28, 26–40.
4. Powell, M. J. & Hansen, D. E. (1989) Protein Eng. 3, 69–75.
5. Pollack, S. J. & Shultz, P. G. (1989) J. Am. Chem. Soc. 111, 1929–1931.
6. Mayforth, R. D. & Quintnas, J. (1990) N. Eng. J. Med. 323, 173–178.
7. Shokat, K. M. & Schultz, P. G. (1990) Ann. Rev. Immunol. 8, 335–363.
8. Janda, K. D., Schloeder, D., Benkovic, S. J., & Lerner, R. A. (1988) Science 241, 1188–1191.
9. Lerner, R. A. & Benkovic, S. J. (1988) BioEssays 9, 107–112.
10. Lerner, R. A. & Tramontano, A. (1988) Sci. Am. 258, 58–70.
11. Schmeck, H. M. (1987) N. York Times, Jan. 27.
12. Scott, A. (1987) N. Scientist, Feb. 12, p. 31.
13. Marx, J. L. (1986) Science 234,1497–8.
14. Baum, R. (1987) Chem. Eng. News 65, 30–33.
15. Kahne, D. & Still, W. C. (1988) J. Am. Chem. Soc. 110, 7529–7534.
16. Tramontano, A., Janda, K. D., & Lerner, R. A.(1986) Science 234, 1566–1569.
17. Tramontano, A., Ammann, A. A., & Lerner, R. A. (1988) J. Am. Chem. Soc. 110, 2282–2286.

18. Teraishi, K., Saito, M., Fujii, I., & Nakamura, H. (1992) Tet. Lett. 33, 7153–7156.
19. Laidler, K. J. (1987) in Chemical Kinetics, Harper & Row, New York, p. 113.
20. Iverson, B. L. & Lerner, R. A. (1989) Science 243, 1184–1188.
21. Gibbs, R. A., Taylor, S., Benkovic, S. J. (1992) Science 258, 803–805.
22. Paul, S., Volle, D. J., Beach, C. M., Johnson, D. J., Powell, M. J., & Massey, R. J. (1989) Science 244, 1158–1162.
23. Carpenter, F. H. (1960) J. Am. Chem. Soc. 82, 1111–1112.
24. Laidler, K. J. (1963) in Reaction Kinetics, Pergamon Press, New York, pp. 42–43.
25. Jencks, W. P. (1969) in Catalysis in Chemistry and Enzymology, McGraw-Hill, New York, pp. 193–194.
26. Eipper, B. A., Stoffers, D. A., & Mains, R. E. (1992) Ann. Rev. Neurosci. 15, 57–85.
27. Kreil, G. (1980) in The Enzymology of Post-Translational Modification of Proteins (Vol. 2), Academic Press, New York, pp. 41–51.
28. Mains, R. E., Eipper, B. E., Glembotski, C. C., Dores, R. M. (1983) 6, 229–235.
29. Gray, C. H. & James, V. H. T., Eds. (1983) in Hormones in Blood, Vol. 5, Academic Press, New York, p.42.
30. Zaidi, M., Moonga, B. S., Bevis, J. R., Bascal, Z. A., & Breimer, L. H. (1990) Crit. Rev. Clin. Lab. Sci. 28, 109–174.
31. Rovero, P., Giuliani, S., & Maggi, C. A. (1992) Peptides 13, 1025–1027.
32. Gallerand, J. C., Fulcrand, P., Bali, J. P., Rodriguez, M., Magous, R., Laur, J., & Martinez, J. (1992) Peptides 13, 519–525.
33. Gray, C. H. & James, V. H. T., Eds. (1983) in Hormones in Blood, Vol. 5, Academic Press, New York, pp. 200–201.
34. Viallet, J. & Ihde, D. C. (1991) Crit. Rev. Onc./Hem. 11, 109–135.
35. Giacchetti, S., Gauville, C., deCremoux, P., Bertin, L., Berthon, P., Abita, J. P., Cuttitta, F., & Calvo, F. (1990) Int. J. Cancer 46, 293–298.
36. Mulshine, J., Avis, I., Carrasquillo, B., Merchant, C., Boland, C., Perentesis, P., Reynolds, J., Larson, S., Treston, A., Scott, F., Kasprzyk, P., Johnson, B., lhde, D., Gazdar, A., Cuttitta, F., & Minna, J. (1990) Proc. Am. Soc. Clin. Oncol. 9, 230.
37. Shipp, M. A., Tarr, G. E., Chen, C.-Y., Switzer, S. N., Hersh, L. B., Stein, H., Sunday, M. E., & Reinherz, E. L. (1991) Proc. Natl. Acad. Sci., USA 88, 10662–10666.
38. Mahmoud, S., Staley, J., Taylor, J., Bogden, A., Moreau, J. P., Coy, D., Avis, I., & Cuttitta, A. (1991) Cancer Res., 51, 1798–1802.
39. Davis, T. P. Crowell, S., Taylor, J., Clark, D. L., Coy, D., Staley, J., & Moody, T. W. (1992) Peptides 13, 401–407.
40. Jensen, R. T. & Coy, D. H. (1991) Trends Pharm. Sci. 12, 13–19.
41. Malikayil, J. A., Edwards, J. V., & McLean, L. R. (1992) Biochemistry 31, 7043–7049.
42. Clavell, L. A., Gelber, R. D., Cohen, H. J., Hitchcock-Bryan, S., Cassady, J. R., Tarbell, N. J., Blattner, S. R., Tantravahi, R., Leavift, P., & Sallan, S. E. (1986) N. Eng. J. Med. 315, 657–663.
43. Cuttitta, F., Carney, D. N., Mulshine, J., Moody, T. W., Fedorko, J., Fischler, A., & Minna, J. D. (1985) Nature 316, 823–826.
44. Gazdar, A. F. (1990) Curr. Opin. Oncol. 2, 321–327.
45. Senter, P. D., Wallace, P. M., Svensson, H. P., Vrudhula, V. M., Kerr, D. E., Hellstrom, I., & Hellstrom, K. E. (1993) Bioconj. Chem. 4, 3–9.
46. Ajayaghosh, A. & Pillai, V. N. R. (1990) J. Org. Chem. 55, 2826–2829.
47. Hammer, R. P., Albericio, F., Gera, L., & Barany, G. (1990) Int. J. Peptide Protein Res. 36, 31–45.
48. Bongers, J., Felix, A. M., Campbell, R. M., Lee, Y., Merkler, D. J., & Heimer, E. P. (1992) Peptide Res. 5, 183–189.
49. Ray, M. V. L., Van Duyne, P., Bertelsen, A. H., Jackson-Matthews, D. E., Sturmer, A. M., Merkler, D. J., Consalvo, A. P., Young, S. D., Gilligan, J. P., and Shields, P. P. (1993) BioTechnology 11, 64–70.
50. Hendriksen, D. B., Breddam, K., Moller, J., & Buchardt, 0. (1992) J. Am. Chem. Soc. 114, 1876–1877.
51. Saviano, G., Temussi, P. A., Motta, A., Maggi, C. A., & Rovero, P. (1991) Biochemistry 30, 10175–10181.
52. Nawa, H., Doteuchi, M., Igano, K., louye, K., & Nakanishi, S. (1984) Life Sci. 34, 1153–160.
53. Russell, A. J. & Klibanov, A. M. (1990) Biochem. Soc. Trans. 17, 1145.
54. Russell, A. J. & Klibanov, A. M. (1988) J. Biol. Chem. 263, 11624–11626.
55. Russell, A. J., Trudel, L. J., Skipper, P. L., Groopman, J. D., Tannenbaum, S. R., & Klibanov, A. M. (1989) Biochem. Biophys. Res. Commun. 158, 80–85.
56. Ashley, J. A. & Janda, K. D. (1992) J. Am. Chem. Soc. 57, 6691–6693.
57. Benkovic, S. J., Napper, A. D., & Lerner, R. A. (1988) Proc. Natl. Acad. Sci., USA 85, 5355–5358.
58. Janda, K. D., Lerner, R. A., & Tramontano, A. (1988) J. Am. Chem. Soc. 110, 4836–4837.

What is claimed is:

1. A catalytic antibody which enhances the rate of hydrolysis of an unactivated primary amide bond, wherein the antibody is produced by a method comprising the steps of:

(i) immunizing an animal with a composition comprising a hapten comprising a compound of the formula:

$$R_1-Y-NH-CH-(R_2)-X$$

wherein $R_1$ is H or branched or a linear, substituted or unsubstituted $C_{1-21}$ alkyl, alkene or alkyne, Y is a polypeptide, $R_2$ is an amino acid side chain, and X is selected from the group consisting of $-P(O)(CH_3)(OH)$, $-P(O)(OH)(OCH_3)$, and $-C(O)(CF_3)$;

(ii) removing antibody-producing lymphocytes from said animal; and (iii) fusing the lymphocytes with myeloma cells and thereby producing hybridoma cells producing the antibody.

2. A catalytic antibody of claim 1 wherein said primary amide bond is contained in a molecule selected from the group consisting of a polypeptide, a C-terminal carboxamide, a side chain of asparagine or glutamine, calcitonin, a calcitonin-gene-related peptide, gastrin, and a bombesin-like peptide.

3. A catalytic antibody which enhances the rate of hydrolysis of a primary amide bond, wherein the antibody is produced by a method comprising the steps of:

(i) raising antibodies against a hapten comprising a compound of the formula:

$$R_1\text{—}Y\text{—}NH\text{—}CH\text{—}(R_2)\text{—}X$$

wherein $R_1$ is H or branched or linear, substituted or unsubstituted $C_{1-21}$ alkyl, alkene or alkyne, Y is a polypeptide, $R_2$ is an amino acid side chain, and X is selected from the group consisting of —P(O)(CH$_3$)(OH), —P(O)(OH)(OCH$_3$), and —C(O)(CF$_3$);

(ii) immobilizing said antibodies;

(iii) adding a substrate to said antibodies; and (iv) identifying antibodies capable of catalyzing the conversion of said substrat to a product.

4. A catalytic antibody of claim 3 wherein the antibodies are concentrated and purified after step (i).

* * * * *

UNITED STATES PATENT AND TRADEMARK OFFICE
CERTIFICATE OF CORRECTION

PATENT NO. : 6,479,265 B1
DATED : November 12, 2002
INVENTOR(S) : Napper et al.

It is certified that error appears in the above-identified patent and that said Letters Patent is hereby corrected as shown below:

Column 3,
Line 66, change "(i)" to -- (I) --

Column 4,
Line 11, change "comound" to -- compound --
Lines 44, 56 and 60, change "(ii)" to -- (II) --

Column 7,
Line 60, change "derection" to -- direction --

Column 8,
Table I, line 33, change "GiA" to -- G1A --
Line 58, change "Table 11" to -- Table II --

Column 11,
Lines 10 and 33, change "e-Amino-n-caproic" to -- ε-Amino-n-caproic --
Lines 16-17, change "(1 979)" to -- (1979) --

Column 14,
Line 15, change "$C_8$" to -- $C_{18}$ --
Line 21, insert -- 3.40 (t, 2H) -- after "3.25 (q, 6H),"

Column 15,
Line 38, change "mixtrue" to -- mixture --

Column 17,
Line 45, delete "." after "with"

Column 21,
Line 35, change "–700° C." to -- –70° C. --

Column 23,
Line 60, change "1was" to -- 1 was --

UNITED STATES PATENT AND TRADEMARK OFFICE
CERTIFICATE OF CORRECTION

PATENT NO.    : 6,479,265 B1
DATED         : November 12, 2002
INVENTOR(S)   : Napper et al.

It is certified that error appears in the above-identified patent and that said Letters Patent is hereby corrected as shown below:

Column 26,
Line 59, change "Ph 9.0" to -- pH 9.0 --

Column 30,
Line 21, change "louye" to -- Iouye --
Line 48, delete "a" before "linear"

Column 32,
Line 5, change "substrat" to -- substrate --

Signed and Sealed this

Eighteenth Day of March, 2003

JAMES E. ROGAN
*Director of the United States Patent and Trademark Office*